United States Patent
Phillips et al.

(10) Patent No.: US 10,395,328 B2
(45) Date of Patent: Aug. 27, 2019

(54) VIRTUAL PROFESSIONALS COMMUNITY FOR CONDUCTING VIRTUAL CONSULTATIONS WITH SUGGESTED PROFESSIONALS

(75) Inventors: Clinton Glen Phillips, Houston, TX (US); Brenton Grant Phillips, Houston, TX (US)

(73) Assignee: Innovation Specialists LLC, Houston, TX (US)

(*) Notice: Subject to any disclaimer, the term of this patent is extended or adjusted under 35 U.S.C. 154(b) by 653 days.

(21) Appl. No.: 13/461,686

(22) Filed: May 1, 2012

(65) Prior Publication Data

US 2013/0297324 A1 Nov. 7, 2013

(51) Int. Cl.
| | | |
|---|---|---|
| G06F 19/00 | (2018.01) | |
| G06Q 10/10 | (2012.01) | |
| G06Q 30/02 | (2012.01) | |
| G16H 40/20 | (2018.01) | |
| G06Q 30/06 | (2012.01) | |
| G06Q 50/22 | (2018.01) | |

(52) U.S. Cl.
CPC .......... *G06Q 50/22* (2013.01); *G06Q 10/10* (2013.01); *G06Q 30/02* (2013.01); *G06Q 30/06* (2013.01); *G16H 40/20* (2018.01); *G06F 19/3418* (2013.01)

(58) Field of Classification Search
CPC ........ G16H 40/20; G06Q 10/10; G06Q 30/02; G06Q 50/22; G06Q 30/06; G06Q 10/06398
See application file for complete search history.

(56) References Cited

U.S. PATENT DOCUMENTS

| | | |
|---|---|---|
| 4,648,037 A | 3/1987 | Valentino |
| 5,864,685 A | 1/1999 | Hagan |
| 6,235,176 B1 | 5/2001 | Schoen et al. |
| 6,463,471 B1 | 10/2002 | Schoenberg |
| 6,497,657 B2 | 12/2002 | Nunome |
| 6,850,889 B1 | 2/2005 | Zayas |
| 7,113,913 B1 | 9/2006 | Davis et al. |

(Continued)

FOREIGN PATENT DOCUMENTS

| | | |
|---|---|---|
| WO | 2010027633 A2 | 3/2010 |
| WO | 2011159250 A1 | 12/2011 |

*Primary Examiner* — Christopher L Gilligan
(74) *Attorney, Agent, or Firm* — Polsinelli PC

(57) ABSTRACT

Systems and methods for providing a virtual professionals community for conducting virtual consultations with suggested professionals includes receiving, in a server, data associated with a plurality of professionals, including a specialty descriptive of one or more of the plurality of professionals. The server can receive a peer performance rating for one of the plurality of professionals generated by a second of the plurality of professionals. A client can submit, to the server, a search request that includes user-defined search criteria. The server can then search the received data based on the search criteria to select relevant professionals associated with the client's search request. The server can rank the selected relevant professionals based on peer performance ratings and the relevancy of the relevant professional to the search criteria. After ranking the selected professionals, the server can transmit a report of the relevant professionals ordered in the ranking determined by the server.

18 Claims, 21 Drawing Sheets

(56) References Cited

U.S. PATENT DOCUMENTS

| | | | |
|---|---|---|---|
| 7,172,120 B2 | 2/2007 | Schoenberg | |
| 7,412,396 B1 | 8/2008 | Haq | |
| 7,478,049 B2 | 1/2009 | Schoenberg | |
| 7,890,345 B2 | 2/2011 | Schoenberg | |
| 7,937,275 B2 | 5/2011 | Schoenberg | |
| 8,005,734 B1 | 8/2011 | Strech | |
| 8,027,846 B2 | 9/2011 | Schoenberg et al. | |
| 8,029,448 B2 | 10/2011 | Sarel | |
| 8,043,224 B2 | 10/2011 | Sarel | |
| 8,103,524 B1 | 1/2012 | Rogers et al. | |
| 8,457,981 B2 | 6/2013 | Schoenberg | |
| 8,510,128 B2 | 8/2013 | Schoenberg | |
| 8,549,031 B2 | 10/2013 | Schoenberg | |
| 8,600,773 B2 | 12/2013 | Schoenberg | |
| 8,620,678 B2 | 12/2013 | Gotlib et al. | |
| 2001/0037219 A1 | 11/2001 | Malik | |
| 2002/0065682 A1 | 5/2002 | Goldenberg | |
| 2002/0091551 A1 | 7/2002 | Parisi | |
| 2003/0191668 A1 | 10/2003 | Oka et al. | |
| 2004/0030225 A1 | 2/2004 | Nunome | |
| 2004/0111291 A1* | 6/2004 | Dust | G06F 19/328 705/2 |
| 2004/0111298 A1 | 6/2004 | Schoenberg | |
| 2004/0111622 A1 | 6/2004 | Schoenberg | |
| 2005/0049898 A1 | 3/2005 | Hirakawa | |
| 2005/0071202 A1 | 3/2005 | Kendrick | |
| 2005/0125254 A1 | 6/2005 | Schoenberg | |
| 2005/0234745 A1 | 10/2005 | Schoenberg | |
| 2006/0100912 A1 | 5/2006 | Kumar et al. | |
| 2006/0161456 A1* | 7/2006 | Baker | G16H 40/20 705/2 |
| 2006/0241974 A1* | 10/2006 | Chao | G06Q 10/00 705/2 |
| 2007/0150372 A1 | 6/2007 | Schoenberg | |
| 2007/0168233 A1 | 7/2007 | Hymel | |
| 2007/0180026 A1 | 8/2007 | Zayas | |
| 2008/0065414 A1* | 3/2008 | Schoenberg | G06Q 10/109 705/2 |
| 2008/0133290 A1* | 6/2008 | Siegrist | G06Q 10/00 705/2 |
| 2009/0150252 A1 | 6/2009 | Schoenberg | |
| 2009/0259492 A1 | 10/2009 | Cossman | |
| 2009/0276233 A1* | 11/2009 | Brimhall | G06Q 30/02 705/38 |
| 2009/0313076 A1 | 12/2009 | Schoenberg | |
| 2009/0319296 A1 | 12/2009 | Schoenberg | |
| 2010/0070297 A1* | 3/2010 | Kharraz Tavakol | G06Q 10/10 705/2 |
| 2010/0094659 A1 | 4/2010 | Schoenberg | |
| 2010/0121156 A1 | 5/2010 | Yoo | |
| 2010/0131300 A1 | 5/2010 | Collopy et al. | |
| 2010/0131304 A1 | 5/2010 | Collopy et al. | |
| 2010/0131308 A1 | 5/2010 | Collopy et al. | |
| 2010/0222649 A1 | 9/2010 | Schoenberg | |
| 2010/0293007 A1 | 11/2010 | Schoenberg | |
| 2010/0293487 A1 | 11/2010 | Schoenberg | |
| 2011/0105853 A1* | 5/2011 | Rakowski | G06Q 10/10 600/300 |
| 2011/0106593 A1 | 5/2011 | Schoenberg | |
| 2011/0119079 A1 | 5/2011 | Schoenberg | |
| 2011/0125736 A1* | 5/2011 | Dave | G06Q 10/10 707/723 |
| 2011/0137683 A1 | 6/2011 | Schoenberg | |
| 2011/0184763 A1 | 7/2011 | Schoenberg | |
| 2011/0191117 A1 | 8/2011 | Hashim-Waris | |
| 2011/0224998 A1 | 9/2011 | Schoenberg | |
| 2011/0246334 A1 | 10/2011 | Schoenberg et al. | |
| 2011/0264550 A1* | 10/2011 | Fair | G06Q 10/10 705/26.2 |
| 2012/0010518 A1 | 1/2012 | Sarel | |
| 2012/0046969 A1 | 2/2012 | Schoenberg | |
| 2012/0109679 A1* | 5/2012 | Massoumi | G06Q 10/109 705/2 |
| 2012/0116813 A1 | 5/2012 | Schoenberg | |
| 2012/0221355 A1 | 8/2012 | Schoenberg et al. | |
| 2012/0284362 A1 | 11/2012 | Schoenberg | |
| 2012/0310661 A1* | 12/2012 | Greene | G06Q 10/087 705/2 |
| 2013/0018663 A1 | 1/2013 | Schoenberg | |
| 2013/0024365 A1 | 1/2013 | Schoenberg | |
| 2013/0030855 A1 | 1/2013 | Schoenberg | |
| 2013/0035953 A1 | 2/2013 | Schoenberg | |
| 2013/0036153 A1 | 2/2013 | Schoenberg | |
| 2013/0046550 A1 | 2/2013 | Schoenberg | |
| 2013/0054288 A1 | 2/2013 | Schoenberg | |
| 2013/0060576 A1* | 3/2013 | Hamm | G06F 19/00 705/2 |
| 2013/0268411 A1* | 10/2013 | Crafts | G06Q 30/0625 705/26.62 |
| 2013/0275146 A1 | 10/2013 | Schoenberg | |
| 2013/0307918 A1 | 11/2013 | Bulat | |
| 2013/0317838 A1 | 11/2013 | Schoenberg | |
| 2013/0317842 A1 | 11/2013 | Schoenberg | |
| 2013/0317843 A1 | 11/2013 | Schoenberg | |
| 2013/0325500 A1 | 12/2013 | Schoenberg | |
| 2013/0339058 A1 | 12/2013 | Gotlib et al. | |
| 2014/0006058 A1 | 1/2014 | Schoenberg | |

* cited by examiner

| MD.COM | heart diseases — 925  410  405 | Search | browse by specialty | 900 | My Health | 905 | My Doctors | 910 | Cart [1] — 915 | Mary |

400 — 920
415 — 505
<< Back — 915

Book Doctor — 925
John Smith MD — 930
Current time: 06:57 AM Thu, 04/12/2012 [autodetected] — 935    change? — 940

Select one or more appointments to book

<    Apr 2012 to May 2012    >

Fri, 04/13/2012 (3 appts)
    01:00 AM
    01:20 AM — 955
    01:40 AM

950

Remove From Cart — 965
Add To Cart — 960
Add To Cart

Check Out >>> — 970

Or fill out the request form below for an appointment  ---- Requesting Appointments: ---- 975

1. Choose a date — 945
   946

| Apr / 2012 |
| Su Mo Tu We Th Fr Sa |
|              1  2  3  4  5  6  7 |
| 8  9  10 11 12 13 14 |
| 15 16 17 18 19 20 21 |
| 22 23 24 25 26 27 28 — 947 |
| 29 30 |

949

2. Choose time(s) for:
04/12/2012
☐ Morning
☐ Afternoon — 977
☐ Evening

3. Repeat for multiple dates — 980

Note: Request times are in US time. Requested times may be different at the specialist's location.

Send Request — 985

MD.COM 1600                          1220 — Activity  Appointments (1)  Inbox (5)  Dr. Smith
Account    General   Search Criteria   Financial   Settings           1210      1205
                                       1215
Appointment Rate
Rate per 20 min  1605   1610    1615
$ [173]  1630           1620
     1632           1635

$3 malpractice coverage                                         1637    1625

There is no catch. By selecting "opt in" at the bottom of the screen, you will elect to have $3 withheld from each of your sessions. This will, provide you with $1,000,000 of liability coverage. Imagine that, malpractice insurance with no paperwork, no wasting time, no hassle, for just a few dollars.

It you would like to take part in our revolutionary insurance program, all you have to do is agree to terms by selecting the box below and your "premium" of $3 per session will be automatically withheld.

By opting in I agree to the following terms

- Insurance coverage for PROFESSIONAL MEDICAL MALPRACTICE LIABILITY is afforded only to those physicians who agree to opt into this optional insurance program.
- Coverage is IN EXCESS to any medical malpractice coverage that such physician may have.
- Policy limits are $1 million per claim and $3 million annual aggregate for ALL claims that may be brought against ALL physicians in the program. In other words all Physicians share the $3 million annual aggregate limit.
- Coverage is for claims worldwide however it will only respond to claims brought within the United States.
- The policy is on a "claims made" form, meaning that it will afford coverage only while the coverage is in force and claims submitted on a timely basis.
- Any incident or potential claim must be submitted to MD.COM immediately upon knowledge of such claim or potential claim.

⦿ Opt in       ○ Opt out
   1640           1645

[Save]  Banking Details
 1650

VIRTUAL PROFESSIONALS COMMUNITY FOR CONDUCTING VIRTUAL CONSULTATIONS WITH SUGGESTED PROFESSIONALS

FIELD OF TECHNOLOGY

The present disclosure relates generally to virtual communities, and more specifically to systems and methods for establishing professional communities that allow clients to search for and conduct virtual consultations with professionals.

BACKGROUND

With the proliferation of the Internet and World Wide Web, virtual communities have increased and become popular. Virtual communities allow a social network of individuals to interact through specific media, such as web-based message boards and email. Some virtual communities have also connected individuals through videoconferencing.

Videoconferencing allows two or more locations to communicate by simultaneous two-way video and audio transmissions. Videoconferencing uses audio and video telecommunications to bring people at different sites together. For example, videoconferencing can be utilized for a conversation between people in private offices (point-to-point) or involve several (multipoint) sites in large rooms at multiple locations. Besides the audio and visual transmission of meeting activities, some videoconferencing technologies allow participants to share documents and display information on shared screens.

Some videoconference systems have been utilized to conduct virtual meetings between doctors and their patients. However, such systems have been utilized with established doctor-patient relationships. In other words, such systems have been implemented in where a doctor and a patient have already established a doctor-patient relationship or already have a relationship through a health insurance network.

BRIEF DESCRIPTION OF THE DRAWINGS

In order to describe the manner in which the features of the disclosure can be obtained, a more particular description of the principles briefly described above will be rendered by reference to specific examples thereof which are illustrated in the appended drawings. Understanding that these drawings depict only example embodiments of the disclosure and are not therefore to be considered to be limiting of its scope, the principles herein are described and explained with additional specificity and detail through the use of the accompanying drawings in which:

FIGS. 4-11 and 14 are example screenshots of a graphical user interface presented to a client of the virtual professionals community, in accordance with an example embodiment of the present disclosure;

FIGS. 12, 13 and 15-17 are example screenshots of a graphical user interface presented to a professional of the virtual professionals community, in accordance with an example embodiment of the present disclosure;

DETAILED DESCRIPTION

Figure 1:
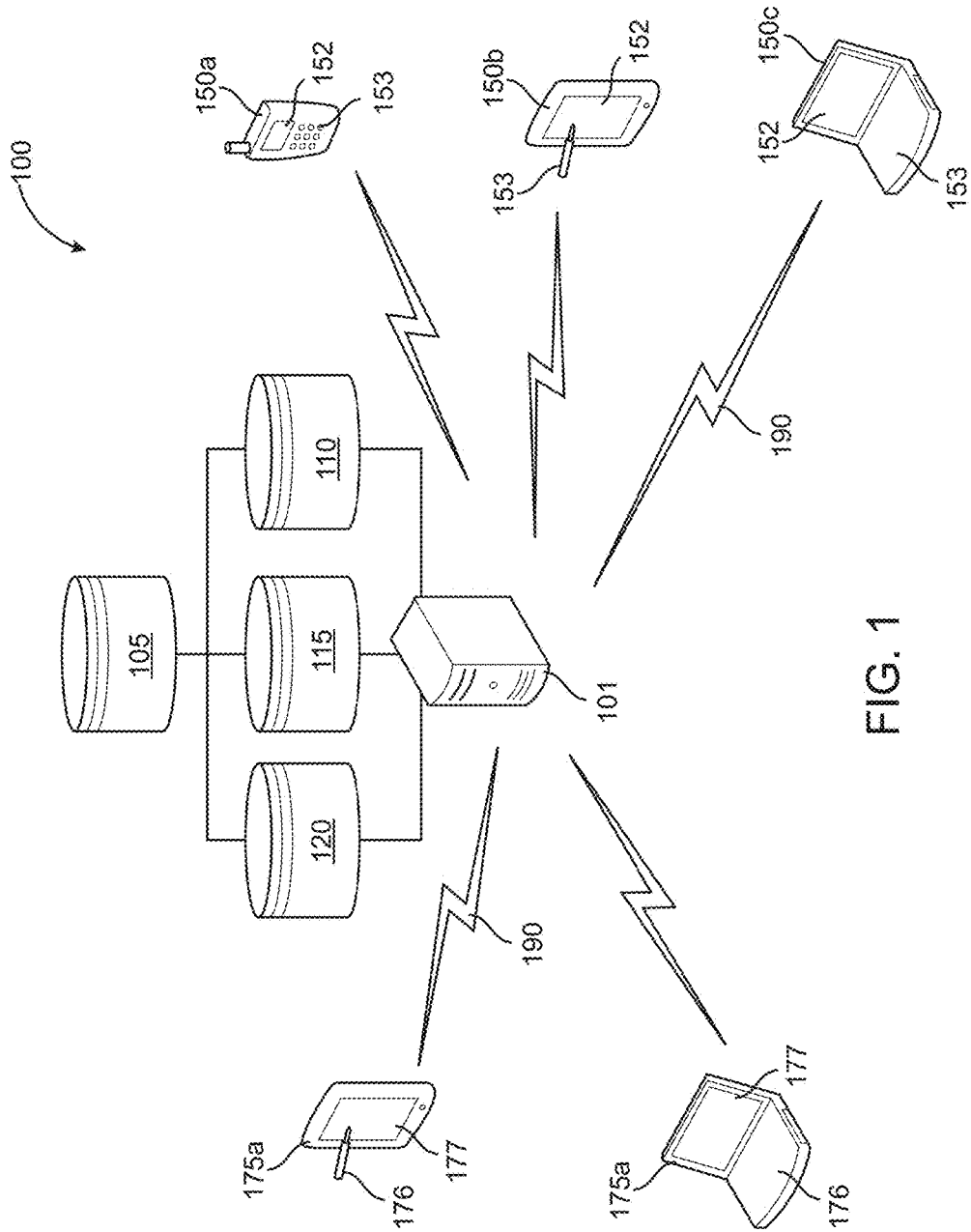
FIG. 1 is a diagram of an example system for providing a virtual professionals community for conducting virtual consultations with suggested professionals, in accordance with an example embodiment of the present disclosure.

Various examples of the disclosure are discussed in detail below. While specific implementations are discussed, it should be understood that this is done for illustration purposes only. A person skilled in the relevant art will recognize that other components and configurations may be used without parting from the scope of the disclosure.

Several definitions that apply throughout this document will now be presented. The phrase "coupled" is defined as connected, whether directly or indirectly through intervening components and is not necessarily limited to physical connections. Coupled devices are devices which are in signal communication with one another.

The term "electronic device" is defined as any device that is capable of at least accepting data, transmitting data, and executing commands. For example, electronic devices can include, but are not limited to, portable communication devices, mobile communication devices, mobile computers, smartphones, computing pads, tablet computers, personal computers, desktop computers, laptop computers, netbooks, servers, routers, set-top phones, or other electronic devices capable of at least accepting data, transmitting data, and executing commands.

The term "client" is defined as a customer, client, or end user who searchers for professionals for virtual consultations.

According to one non-limiting example of a system and method of providing a virtual professionals community for conducting virtual consultations with suggested professionals can include receiving, at a server, data associated with a plurality of professionals, said data including a specialty descriptive of one or more of said plurality of professionals. A peer performance rating can also be received at the server for one of said plurality of professionals. The peer performance rating can be generated by a second professional from the plurality of professionals. The server can create a database comprising data associated with the plurality of professionals, including performance evaluations of the professionals, peer performance ratings associated with the professionals and search terms associated with at least one or more of symptoms and problems treated by or considered by the professionals, specialties of the professionals, and credentials of the professionals. The server can also receive a search request for selecting relevant professionals. The search request can include search criteria by which the server can suggest one or more relevant professionals to a client device (for example, a patient or a client's device). In response to receiving the search request, the server can conduct a search of the received data based on the search criteria of the search request. In conducting the search, the server can determine, select, or suggest relevant professionals to the client who transmitted the search request to the server. After determining or selecting relevant professionals to suggest to the client, the server can rank the selected relevant professionals. For example, the server can rank the selected relevant professionals based on the peer performance ratings and the search request that includes the search criteria. In another embodiment, the server can further rank the selected relevant professionals based on a performance evaluation. The performance evaluation can be received by the server from prior clients of the professional. After the server ranks the selected relevant professionals, the server can transmit a report of the relevant professionals. For example, the server can transmit to an electronic device of the client the report of the relevant professionals from which the client can select or choose one or more of the relevant professionals for a virtual consultation.

The server can then receive a selection by the client, wherein the selection is indicative of a professional with whom the client would like to consult. In response to the selection, the server can transmit data to the client, wherein the data includes a schedule associated with the professional. The schedule including the availability of the professional for consultations. The server can also receive an appointment request for an appointment from the client. For example, the client can select an open or available timeslot listed on the professional's schedule. In another embodiment, the client can request a new timeslot that is not listed on the professional's schedule. In response to receiving the appointment request for the appointment, the server can transmit the appointment request to one or more electronic devices of the professional.

The professional, via one or more of his or her electronic devices, can transmit confirmation data to the server indicative of the professional's acceptance or rejection of the appointment request. If the professional accepts the appointment request, the server can establish an appointment interface (for example, a virtual consultation) between an electronic device of the professional and an electronic device of the client at the timeslot selected by the client and accepted by the professional. At a predetermined time before the time associated with the timeslot selected by the client and accepted by the professional, the server can transmit a notification to the professional. The notification can include access to the appointment interface (for example, a hyperlink or other access point for accessing the appointment interface). The notification can also include a selectable option corresponding to a professional insurance coverage. The professional insurance coverage can be based at least in part on the appointment request submitted or transmitted by the client. The professional insurance coverage can also include a coverage period corresponding to a duration of the appointment interface. The professional may select an option corresponding to an acceptance or a rejection of the professional insurance coverage. In response to the professional's selection, the server can grant access to the appointment interface to at least one of the electronic device of the professional and the electronic device of the client.

When access is granted to the appointment interface to at least one of the electronic device of the professional, the professional and client can conduct a virtual consultation over the appointment interface. According to a non-limiting embodiment of the present disclosure, the duration of the appointment interface can be a predetermined duration (for example, twenty (20) minutes). In other embodiments, the duration can be determined or controlled by the electronic device of the professional. For example, in response to a detection that the electronic device of the professional has disconnected from or terminated the professional's electronic device connection to the appointment interface, the appointment can be terminated. That is, the connection between the electronic device of the client and the appointment interface can be terminated in response to a detection of the disconnection of the professional's electronic device with the appointment interface.

Example embodiments and implementations of the virtual professionals community for conducting virtual consultations with suggested professionals will be described in further detail with respect to FIGS. 1-21. While the following figures, embodiment, and implementations are described in relation to a virtual medical professionals community in which past, current, and potential or future patients can connect with medical professionals (such as doctors, dentists, and nurses) for virtual consultations, it will be appreciated that the virtual professionals community for conducting virtual consultations with suggested professionals can be applied to other professional communities, such as legal professional communities, financial professional communities, psychotherapeutic professional communities, or any other professional community in which clients and professionals can benefit from virtual consultations. Those of ordinary skill in the art will also appreciate that the professionals and the clients of the virtual professional communities can be professionals and clients who have registered as and agreed to be members of the virtual community. The professionals can become members by invitation by any one of an administrator of the virtual community, a client who is a member of the virtual professionals community, a peer professional who is a member of the virtual professionals community. In other embodiments, the professional can request membership to the virtual professionals community, subject to approval by any one of the administrator of the virtual professionals community, clients who are members of the virtual professionals community, and other professionals who are members of the virtual professionals community. Similarly, clients can be become members of the virtual professionally by invitation or requesting membership.

FIG. 1 is a block diagram of a system 100 for providing a virtual professionals community for conducting virtual consultations with suggested professionals. In FIG. 1, the virtual professionals community system 100 can include a server 101, one or more client electronic devices 150*a-c*, and one or more professional electronic device 175*a-b*. The virtual professionals community can be accessed by nay one of the one or more client electronic devices 150*a-c* and one or more professional electronic device 175*a-b* by a web browser, the Internet, the World Wide Web, an intranet, a web-based application, a smartphone application, an electronic pad application, or any other application executable on an electronic device via wireless or wired communication interface.

The server 101 can be a system of servers. In other embodiments, the server 101 can be a single central server 101. In still other embodiments, the server 101 can be a web-based server, a webserver, a cloud-based server, a backend server associated with a website or application of the virtual professionals community. Although not illustrated in FIG. 1, the server 101 can include at least one processor. In other embodiments, the server 101 can include or a processing system including one or more processors. The processor (not shown) can be configured to receiving and processing data and requests from the one or more client electronic devices 150*a-c* and the one or more professional electronic device 175*a-b* and executing processes associated with suggesting professionals to the one or more client electronic devices 150*a-c* and establishing appointment interfaces between from the one or more client electronic devices 150*a-c* and the one or more professional electronic device 175*a-b*.

Also illustrated in FIG. 1, the server 101 can be communicatively coupled to a professionals database 105. The professionals database 105 can be a non-transitory or transitory computer-readable storage medium. The professionals database 105 can include data associated with a plurality of professionals. For example, the professionals database 105 can include educational data, certification data, specialty data, award and recognition data, publication data, biographical data, institution affiliation data (for example, universities, hospitals, clinics, colleges, courts, financial institutions, or any other institutions with which professionals can be associated), user credentials (for example, user names, passwords, contact information) or any other information and data associated with professionals.

The server can also be communicatively coupled to a search terms database 110. The search terms database 110 can include a glossary of terms associated with the professionals of the professionals database 105. For example, the terms of the search terms database 110 can be associated with one or more professionals of the professionals database 105 (for example, by key value pairs). In at least one embodiment, where the virtual community is a virtual community connecting doctors and medical professionals with current, prior, and future patients, the search terms database 110 can include search terms associated with symptoms and problems that patients can have. For example, the search terms associated with the symptoms and problems can include terminology typically utilized by the professionals and colloquial terminology that are synonymous with the professionals" terminology. In at least one embodiment, the search terms of the search terms database 110 can be added to the search terms database 110 by the proprietor of the server 101, by third parties associated with the proprietor of the server 101, by medical professionals contracted by the proprietor of the server 101, by web-crawlers or devices configured to search medical references, publications, and public medical records for search terms associated with symptoms and problems of clients (for example, patients). In at least one embodiment, search terms associated with symptoms and problems that are associated with one professional's specialty can be paired with the professional's data stored in the professional database 105, such that when a search query for professionals who can treat the queried symptoms and problems can return the professional's data that is pairs with the queried search terms.

Also illustrated in FIG. 1, the server 101 can be communicatively coupled with a peer review database 115. The peer review database 115 can include data representing peer reviews of at least some of the professionals stored in the professionals database 105. For example, the peer review database 115 can include data representing one or more peer performance reviews of a professional associated with professional data stored in the professionals database 105, wherein the peer performance review submitted by other professionals who may or may not have professional data stored in the professionals database 105. In at least one example, the peer review can include critiques, reviews, and comments regarding the credentials and performance of a professional having data stored in the professionals database 105. For example, the peer performance reviews can be an electronic survey, an electronic peer performance rating, an electronic comment card, or any other electronic representation of a peer performance review that can be stored in and queried from the peer review database 115. It will be appreciated that the peer performance reviews of the peer review database 115 are generated by other professionals associated with the professionals having data stored in the professionals database 105. For example, the other professionals who generate the peer performance reviews can include colleagues, former professors, former classmates, co-workers, and other professionals having knowledge of the professional being reviewed and having data stored in the professionals database. In another embodiment, the peer performance reviews can be generated by colleagues, former professors, former classmates, co-workers, and other professionals having first-hand knowledge of the professional being reviewed and having data stored in the professionals database. The peer performance review data stored in the peer review database 115 can be paired with the data stored in the professionals database 105, such that the professional data stored in the professionals database 105 can be paired or retrieved when corresponding peer performance review data is retrieved. For example, if a search containing search criteria for a professional is executed, the text of the peer performance review stored at the peer review database 115 can be searched for data matching the search criteria. If a peer performance review datum matches the search criteria, the professional data corresponding to the peer performance review datum (for example, the professional data of the professional whom the peer performance review is about) can be retrieved from the professionals database 105. By providing a peer performance review, clients searching the virtual professionals community for professionals with whom to conduct virtual consultations can review the peer performance reviews to arrive at an informed decision about which professional to conduct the virtual consultation. Additionally, the peer performance reviews can provide clients with reassurance that the professional(s) with whom the client will conduct a virtual consultation is a legitimate professional who is qualified or has the credentials and experience to evaluate and consult with the client regarding the client's specific symptoms and problems.

In FIG. 1, the server 101 can also be communicatively coupled with a client review database 120. The client review database 120 can include data representing client reviews of the performance of at least some professionals having data stored in the professional database 105, where the performance reviews are generated by current, past, or both current and past clients or patients of the professionals having data stored in the professional database 105. In at least one example, the client review can include critiques, reviews, and comments regarding the credentials and performance of a professional having data stored in the professionals database 105. For example, the client reviews can be an electronic survey, an electronic peer performance rating, an electronic comment card, or any other electronic representation of a client performance review that can be stored in and queried from the client review database 120. It will be appreciated that the client reviews of the client review database 120 are generated by current, past, or both current and past clients having first-hand knowledge of the professional being reviewed and having data stored in the professionals database. The client review data stored in the client review database 120 can be paired with the data stored in the professionals database 105, such that the professional data stored in the professionals database 105 can be paired or retrieved when corresponding client review data is retrieved. For example, if a search containing search criteria for a professional is executed, the text of the client review data stored at the client review database 120 can be searched for data matching the search criteria. If a client review datum matches the search criteria, the professional data corresponding to the client review datum (for example, the professional data of the professional whom the client review datum is about) can be retrieved from the professionals database 105. By providing a client review, future or potential clients searching for professionals with whom to conduct virtual consultations can review the client reviews to arrive at an informed decision about which professional to conduct the virtual consultation. Additionally, the client reviews can provide clients with reassurance that the professional(s) with whom the client will conduct a virtual consultation is a legitimate professional who is qualified or has the credentials and experience to evaluate and consult with the client regarding the client's specific symptoms and problems.

In FIG. 1, a client can access the virtual professionals community associated with the server 101 (for example, hosted by the server 101) via any one of the client's client electronic devices 150a-c. For example, the client's client electronic devices 150a-c can include a smartphone 150a, an electronic table 150b, and a portable computer 150c. However, the client electronic device 150a-c can be any other type of electronic device including portable communication devices, mobile communication devices, mobile computers, smartphones, computing pads, electronic pads personal computers, desktop computers, laptop computers, netbooks, servers, routers, set-top phones, or other electronic devices capable of at least accepting data, transmitting data, and executing commands. As the client can access the virtual professionals community from a plurality of electronic devices 150a-c, the client can search for, select, and conduct virtual consultations with a professional of the virtual professionals community at any location convenient for the client. That is, the client can conduct a virtual consultation with a professional remote from the professional. The electronic devices can also be configured to with audio and visual hardware (for example speakers, microphones, video cameras, display screens 152, and other audio-visual hardware) by which the clients operating the client electronic device 150a-c can conduct virtual consultations. The client devices 150a-c can also include input interfaces 153 by which user of the client device 150a-c can enter or input data. For example, the input interfaces 153 can include but are not limited to keyboards, touchscreens, touch sensitive displays, voice command interface, gaze tracking interfaces, motion input interfaces, or any other input interface by which user inputs can be entered. Also, as illustrated in FIG. 1, each of the client electronic devices 150a-c can be communicatively coupled to the server 101 via a network 190. For example, the network 190 can include including an intranet, the Internet, a cellular network, a local area network, a near field communication network, a cloud-based network, or any other such network or combination thereof. Components used for such a system can depend at least in part upon the type of network and/or environment selected. Protocols and components for communicating via such a network are well known and will not be discussed herein in detail. Communication over the network can be enabled by wired or wireless connections, and combinations thereof. In this example, the network 190 includes the Internet, as the environment includes a web-based server 101 for receiving requests and serving content in response thereto, although for other networks an alternative device serving a similar purpose could be used as would be apparent to one of ordinary skill in the art. While FIG. 1 illustrates a plurality of electronic device 150a-c associated with one client, it will be appreciated that a plurality of clients, each having one or more electronic devices, can be communicatively to the server 101 to access the virtual professionals community.

A professional can access the virtual professionals community associated with the server 101 (for example, hosted by the server 101) via any one of the professional's professional electronic devices 175a-b. For example, the professional's professional electronic devices 175a-b can include an electronic table 175a and a portable computer 175b. However, the professional electronic device 175a-b can be any other type of electronic device including portable communication devices, mobile communication devices, mobile computers, smartphones, computing pads, electronic pads personal computers, desktop computers, laptop computers, netbooks, servers, routers, set-top phones, or other electronic devices capable of at least accepting data, transmitting data, and executing commands. As the professional can access the virtual professionals community from a plurality of electronic devices 175a-b, the professional can respond to any appointment requests from clients and conduct virtual consultations with a client of the virtual professionals community at any location convenient for the professional. That is, the professional can conduct a virtual consultation with a client remote from the client. The electronic devices 175a-b can also be configured to with audio and visual hardware (for example speakers, microphones, video cameras, display screens 177, and other audio-visual hardware) by which the clients operating the professional electronic device 175a-b can conduct virtual consultations. The professional electronic device 175a-b can also include input interfaces 176 by which user of the professional electronic device 175a-b can enter or input data. For example, the input interfaces 176 can include but are not limited to keyboards, touchscreens, touch sensitive displays, voice command interface, gaze tracking interfaces, motion input interfaces, or any other input interface by which user inputs can be entered. Also, as illustrated in FIG. 1, each of the professional electronic device 175a-b can be communicatively coupled to the server 101 via a network 190. For example, the network 190 can include including an intranet, the Internet, a cellular network, a local area network, a near field communication network, a cloud-based network, or any other such network or combination thereof. Components used for such a system can depend at least in part upon the type of network and/or environment selected. Protocols and components for communicating via such a network are well known and will not be discussed herein in detail. Communication over the network can be enabled by wired or wireless connections, and combinations thereof. In this example, the network 190 includes the Internet, as the environment includes a web-based server 101 for receiving requests and serving content in response thereto, although for other networks an alternative device serving a similar purpose could be used as would be apparent to one of ordinary skill in the art. While FIG. 1 illustrates a plurality of professional electronic device 175a-b associated with one professional, it will be appreciated that a plurality of professionals, each having one or more electronic devices, can be communicatively to the server 101 to access the virtual professionals community.

Figure 2:
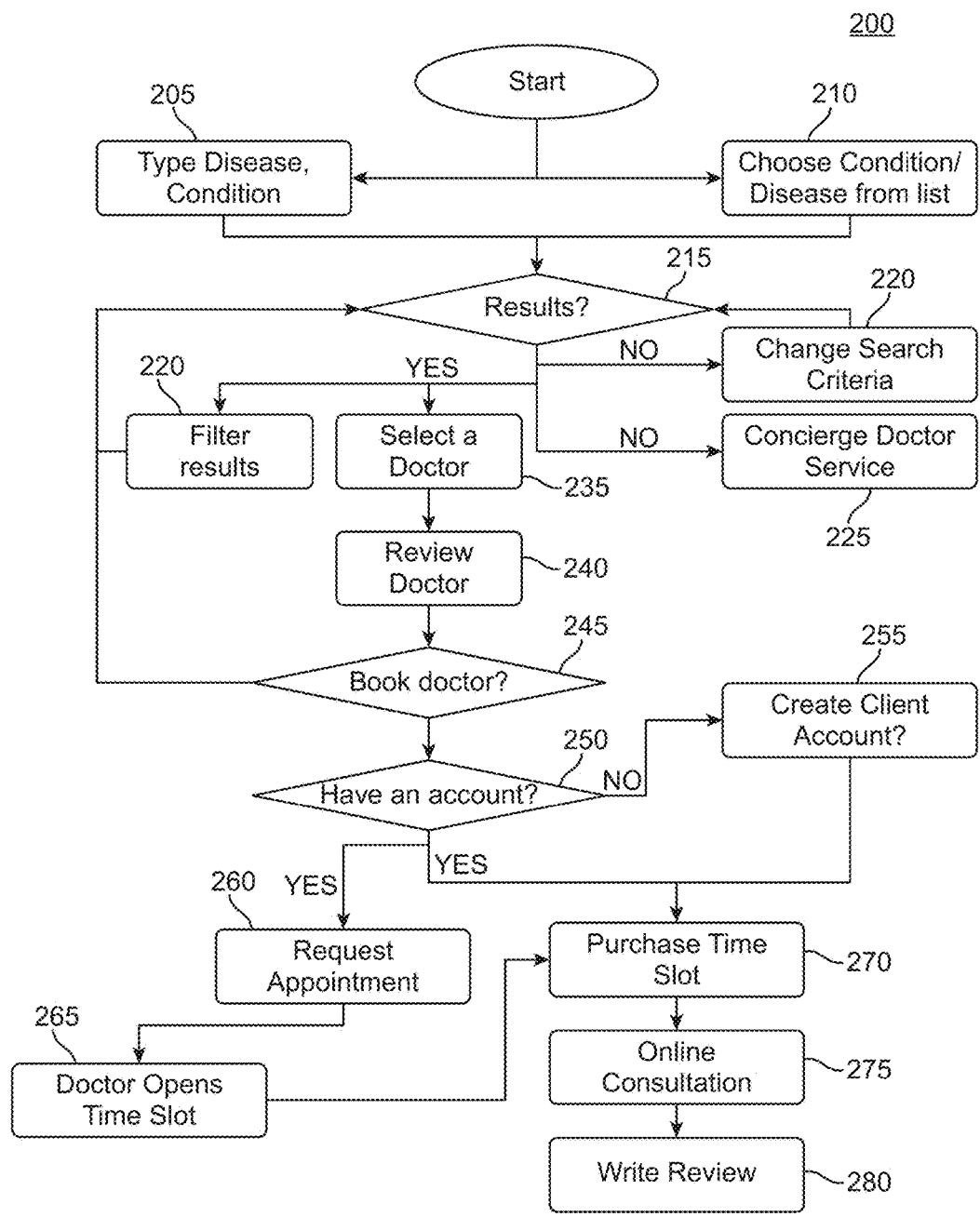
FIG. 2 is a flow chart illustrating an example method of client's execution of a search query for conducting a virtual consultation from the perspective, in accordance with an example embodiment of the present disclosure.

FIG. 2 is a flow chart of a client's interaction with the virtual professionals community of the present disclosure, where the client searches for and requests an appointment for a virtual consultation with a professional of the professional community. Specifically, FIG. 2 illustrates a method 200 associated with a client that is a patient searching for a professional that is a doctor for a medical consultation or evaluation. The method of FIG. 2 is provided by way of example, as there are a variety of ways to carry out the method. Additionally, while the example method 200 is illustrated with a particular order of steps, those of ordinary skill in the art will appreciate that FIG. 2 and the steps illustrated therein can be executed in any order that accomplishes the technical advantages of the present disclosure and can include fewer or more steps than illustrated.

Each block shown in FIG. 2 can represent one or more processes, methods or subroutines, carried out in example method 200. The steps illustrated in FIG. 2 can be implemented in the system 100 illustrated in FIG. 1. Each block shown in FIG. 2 can be carried out by a processor (not shown) of a client electronic device 150*a-c* (which can be one or more processors or one or more processing systems communicatively coupled to the electronic device 150*a-c*) or one or more processors or processing systems of the server 101 illustrated in FIG. 1. Additionally, those of ordinary skill in the art will appreciate that the steps illustrated in FIG. 2 can include instructions of processes stored in a non-transitory computer readable medium communicatively coupled to at least one of the server 101, the client electronic device 150*a-c*, and the professional electronic device 175*a-b*. For purposes of illustration, FIG. 2 will be described from the perspective of the server 101.

In FIG. 2, the server 101 can transmit data to a client's electronic device 150*a-c* to display a graphical user interface 400 (shown in FIG. 4) associated with the virtual professionals community. Via the graphical use interface 400, clients can search for professionals, request suggested professionals, and select professionals with whom to conduct virtual consultations. FIG. 2 illustrates a method 200 by which the client can select a suggested professional and conduct a virtual consultation with a suggested professional of the virtual professionals community.

In FIG. 2, the method 200 can begin at either block 205 or 210 with receiving, at the server 101, a search query. The search query can be at least one of a request for data associated with a professional or a request for a suggested professional. The search query can be manually inputted (block 205) or selected from a predetermined or pre-generated list (block 210).

At block 205, the server 101 can receive, from a patient's client device 150*a-c*, a search query comprising search terms associated with a disease, symptom, or condition manually inputted by a user at the patient's client device 150*a-c*. In at least one embodiment, the search query can also include other search criteria such as a preferred gender of the professional, a preferred city of residence of the professional, a preferred academic background of the professional, preferred board certifications of the professional, preferred geographical location, preferred specializations or professional specialties of the professional, or any other search criteria by which a patient can identify or focus a search query for a desired professional with whom to conduct a virtual consultation.

Alternatively, the server 101 can receive data indicative of a search query selected from a predetermined or pre-generated list, at block 210. For example, the graphical user interface 400 can include a pull-down menu, a drop-down list, a user-selectable hyperlink corresponding to a list of conditions, diseases, symptoms, and other search criteria. The predetermined or pre-generated list (such as a pull-down menu, a drop-down list, a user-selectable hyperlink corresponding to a list of conditions, diseases, symptoms, and other search criteria) can include selectable search terms associated with conditions, diseases, symptoms and problems, and other search criteria such as a preferred gender of the professional, a preferred city of residence of the professional, a preferred academic background of the professional, preferred board certifications of the professional, preferred geographical location, preferred specializations or professional specialties of the professional, or any other search criteria by which a patient can identify or focus a search query for a desired professional with whom to conduct a virtual consultation. The user can select one or more conditions, diseases, symptoms, and other search criteria from the pull-down menu, drop-down list, menu, or predetermined or pre-generated list to form a search query to be executed by a processor of the server 101 of the professionals database 105 and search terms database 110. When the server 101 receives the search query including search criteria at either block 205 of block 210, the method can proceed to block 215.

At block 215, the server 101 can execute a search of the professionals database 105 and the search terms database 110 using the search criteria of the search query to determine whether any professionals match the search criteria of the search query. For example, a processor or processing system communicatively coupled to the server 101 can execute the search of the professionals database 105 and the search terms database 110 using the search criteria of the search query. In executing the search, the processor or processing system of the server 101 can compare the search criteria of the search query to the data stored in the professionals database 105. For example, the search criteria can be compared to the credentials, specialties, education, diseases and symptoms treated, certifications, and other data stored in the professionals database.

In comparing the search criteria to the search terms database 110, the processor communicatively determine whether any of the search terms stored in the search terms database 110 match the search criteria. In at least on embodiment, the search terms of the search terms database 110 can be paired or correlated with one or more professional data stored in the professionals database 105. For example, if the search criteria match a search term of the search term database 110 that is paired with one or more professional data stored in the professionals database 105, the professional data corresponding to the search term can be retrieved from the professionals database 105.

Similarly, the processor or processing system of the server 101 can also execute a search of the client review database 120 and the peer review database 115. For example, the processor or processing system of the server 101 can compare the search criteria of the search query to the data contained in one or both of the client review database 10 and the peer review database 115. If one or both of a client review datum or peer performance review datum match the search criteria of the search query, the professional data corresponding to the professional which the client review datum or the peer performance review datum is about can be retrieved from the professionals database 105. Those of ordinary skill in the art will appreciate that a match between search criteria and data from any one of the professional database 105, the search term database 110, the peer review database, and the client review database 120 can be based on a percentage of matching criteria. For example, a match can be determined if data from any one of the professional database 105, the search term database 110, the peer review database, and the client review database 120 matches a predetermined minimum number of search criteria (for example, set by one or more of the server 101, an administrator of the server 101, the client electronic device 150*a-c*, and the professional electronic device 175*a-b*), a predetermined percentage of search criteria, a majority of the search criteria, or any threshold set by one or more of the server 101, an administrator of the server 101, the client electronic device 150a-c, and the professional electronic device 175a-b to indicate that data from any one of the professional database 105, the search term database 110, the peer review database, and the client review database 120 sufficiently matches a client's search query.

At block 215, if the search executed by the processor or processing system of the server 101 does not return any matching professional data, the method can proceed to either block 220 or block 225. At block 220, data can be transmitted to the client electronic device 150 a-c by which the client electronic device 150a-c can display a selectable option, in the graphical user interface 400 that allows the client to change his or her search criteria. For example, selecting the selectable option to change the search criteria can allow the user to broaden his or her search terms, remove at least one criterion, or otherwise modify his or her search query. At block 225, data can be transmitted to the client electronic device 150 a-c by which the client electronic device 150a-c can display a selectable option, in the graphical user interface 400, that allows the client to initiate a concierge professional service (for example, a concierge doctor server). For example, selection of the concierge professional service can cause the processor or processing system of the server 101 to transmit data to the client electronic device 150a-c or initiate a process on the client electronic device 150a-c by which a assistant icon or character can assist the client in formulating a search query for an appropriate or relevant professional that matches at least some (for example, a majority, all, or a predetermined number or percentage) of the client's search criteria. In other embodiments, selection of the concierge professional service can cause the processor processing system of the server 101 to establish a communication interface between the client's electronic device 150a-c and a concierge's electronic device (not shown). For example, the server 101 can establish a voice call, a videoconference, a chat room, or any other communication interface between the client's electronic device 150a-c and a concierge electronic device, whereby the client can interact and communicate with a concierge to assist the client in searching for an finding a professional who meets at least some of the criteria of the client's search query. In at least one embodiment, the server can establish a live chat with a concierge such that the client can communicate or speak with the concierge to describe his or her symptoms, disease, condition, and other criteria so that the concierge can search or determine an appropriate professional with whom the client can conduct a virtual consultation.

If the server 101 determines that at least some data from any one of the professional database 105, the search term database 110, the peer review database, and the client review database 120, and essentially data associated with a professional of a virtual professionals community, the method can proceed to either block 230 or block 235. At each of blocks 230 and 235, the server 101 can transmit data to the client electronic device 150a-c from which a search results list or a report can be displayed at the client electronic device 150a-c. The search results lists 500 (shown in FIG. 5) can display a list of professional data, retrieved from the professionals database 105, that substantially match the search criteria of the client's search query. The list of professional data can be ranked based at least in part on peer performance reviews (for example, peer performance ratings) and matching criteria of the search query (for example, the search request). In other embodiments, the list of professional data can be further based on a client review rating.

In one non-limiting example embodiment, the server 101 can first rank the professional data matching the search query based on a relevancy rating associated with a number of the professional data matching the search criteria of the client's search query. For example, professional data matching 90% of the search criteria of the client's search query can appear first on the list of the professionals, whereas professional data matching 55% of the search criteria can appear towards an end of the list of professional data. After the professional data matching the client's search query is ranked based on the relevancy rating associated with the number of professional data matching the search criteria of the client's search criteria, the server 101 can then rank the list of professional data based on peer performance reviews. For example, the professional data associated with high peer performance reviews (for example, high peer performance review rankings) can be listed higher on the list of professional data than professional data associated with lower or no peer performance reviews. In one example, where the top two professional data on the list of professional data have a same relevancy rating or a relevancy score indicating that the professional data match a same number of search criteria of the client's search query, the professional data having a higher peer performance review ranking will be listed first followed by the other professional data. After the list of professional data is ranked based on peer performance reviews, the server 101 can optionally rank the list of professional data based on client reviews (for example, client reviews having client review rating). In one example, professional data having a high client review rating can appear higher in the list of professional data than professional data having a lower client review rating. For example, where the second and third professional data of the list of professional data have a same relevancy score and a same peer performance review ranking, the professional data having the higher client review rating will be listed second and the other professional data will be listed third. In other embodiments, the relevancy score associated with the amount of professional data matching search criteria of the client's search query, the peer performance review ranking (or rating), and the client review rating (or ranking) can be weighted and utilized in a ranking algorithm to determine an order in which to list the professional data matching the client's search criteria. Additionally, the ranking of the professional data can be used to determine which professional data to display in the list as professionals whom the server 101 suggests to the client should conduct a virtual consultation.

Those of ordinary skill in the art will appreciate that the relevancy score, the peer performance review ranking (or rating), and the client review rating (or ranking) can be used to exclude professional data from the list of professional data. For example, professional data having a relevancy score, a peer performance review ranking (or rating), and a client review rating (or ranking), or a score based on a combination thereof that falls below or does not meet a predetermined ranking, rating, or score can be excluded from the search results list or report of professional data or can be placed towards a bottom of the list or report of the professional data. For example, each professional data determined to match at least some of the search criteria of the client's search query can have a corresponding ranking score. The ranking score can be based at least on the relevancy score, the peer performance review ranking (or rating), and the client review rating (or ranking). Each of the relevancy score, the peer performance review ranking (or rating), and the client review rating (or ranking) can be weighted. For example, the relevancy score can be weighted more than the client review ranking. In another example, the peer performance review ranking can be weighted more than the client review ranking. After the relevancy score, the peer performance review ranking (or rating), and the client review rating (or ranking) are weighted, the relevancy score, the peer performance review ranking (or rating), and the client review rating (or ranking) can be combined (for example, summed, multiplied, or otherwise combined) to result in a ranking score (for example, a total ranking score). Each of the professional data can then be ranked by their respective ranking scores (for example, the professional data having higher ranking scores appearing towards a top or first on the list or report), and the list or report of search results can be transmitted to the client device 150a-c for display at the client device 150a-c.

After transmitting data to the client device 150a-c for displaying the list or report of professional data the server 101 determines as substantially matching the search criteria of the client's search query (that is, the list of professionals whom the server 101 suggests the client 150a-c should conduct virtual consultations), at block 230, the server 101 can receive data indicative of a client's request to filter the results of the search results list or report of professional data. For example, the client can select a user selectable filter option displayed on the graphical use interface 400 containing the search results lists 500, and a filter request can be transmitted to the server 101. In one example, the filter option can include a request to filter the search results list 500 based on languages spoken by the professional, a gender of the professional, a specialty of the professional, board certifications of the professional, available appointments, a number of publications, a number of client reviews, a number of peer performance reviews, client review rankings, peer review rankings, or any other data or information associated with the professional. Based on the filter request, the server 101 can modify the list of professionals in accordance with the filter request. If no results are available based on the filter request, the method can proceed to blocks 220 or 225, as discussed above. Alternatively, if no filter request is received, the method can proceed to block 235.

At block 235, the server 101 can receive data indicative of a selection of a professional datum listed in the search results list of professionals. For example, the client device 150a-c can select, click on, highlight, or otherwise designate one or more of the professional data listed in the search results list, and a signal indicative of the selection can be transmitted to the server 101. In response to a selection of one or more professional data from the search results list or report of professionals, the server 101 can transmit data to the client device 150a-c for displaying one or more professional profiles 600 including detailed information associated with the respective professional. For example, the professional profile 600 can be a web page, a professional's home page, or other electronic document having detailed information associated with the respective professional. The detailed information can include the professional's credentials, education, biography, interests, treated diseases, peer performance reviews, client reviews, place of work, background, schedule, or any other detailed information associated with the professional. By providing the professional profile(s) 600 at the client device 150a-c, the client can review the detailed information of the professional profile 600 to determine whether the professional is the one with whom the client would like to conduct a virtual consultation.

After receiving a selection of one or more professionals and transmitting data from which the client device 150a-c can display the one or more professional profiles 600, the method 200 can proceed to block 245.

At block 245, the processor processing system of the server 101 can determine whether data indicative of a request to book an appointment with the selected professional has been received from the client device 150a-c. For example, a client can select a user selectable option, displayed on the graphical user interface 400, for booking an appointment with the selected professional. In another embodiment, the client can select an available appointment displayed on a calendar or schedule included in the professional profile 600, as will be described in further detail below. In still another embodiment, the client can select a user selectable option that transmits a request to the server 101 or the associated professional's electronic device 175a-b for an appointment or for an acceptance of an appointment suggested by the client. If a request for an appointment is received at block 245, the method can proceed to block 250.

At block 250 a determination can be made as to whether the client is a member of the virtual professionals community. For example, the server 101 can determine whether the client has an account with the virtual professionals community.

If the server 101 determines that the client does not have an account, the method 200 can proceed to block 255. At block 255, the server 101 can transmit data to the client electronic device 150a-c for displaying an account creation graphical user interface (GUI). For example, the account creation GUI can be an electronic form or an electronic page having a plurality of any one or combination of text entry boxes, selection boxes, dialogue selections, free-form text boxes, pull-down lists, and other input elements by which the client can enter client information to set up an account and become a member of the virtual professionals community. Such information can include the creation of login credentials, financial information, personal information, medical information, prior medical history, prior professional history, credit card information, addresses, phone numbers, email addresses, or any other information for becoming a member of the virtual professionals community. After the server 101 receives the client's information for creating an account at block 255, the method 200 can proceed to block 260 or block 270.

Similarly, if the server 101 determines that the client electronic device 150a-c has an account or is a member of the virtual professionals community, the method can proceed to block 260 or block 270. For example, the server 101 can determine that the client has an account or is a member of the virtual professionals community by requesting login credentials from the client electronic device 150a-c to proceed with booking the appointment. In another embodiment, the client can have been logged in prior to submitting his or her search query.

At block 270, the server 101 can receive a request from a client device 150a-c to purchase an open timeslot in a list of available appointments displayed on or accessible through the professional's profile 600. For example, the client can be presented with a calendar or schedule of the professional's available dates and times for appointments. In one example, the calendar can designate open appointments and times by a first color, unavailable appointments in a second color, and non-designated timeslots in a third color. The non-designated timeslots can correspond to timeslots in which the professional has not designated for appointments but is not busy. The non-designated timeslots can include the timeslots that the professional can open if requested by a client. The non-designated timeslots can also include timeslots reserved for private patients or clients of the professional. If the client selects one of the open appointments, the server 101 can transmit data to the client electronic device 150a-c for displaying a purchase page by which the client can purchase the selected timeslot. For example, the purchase page can be a checkout page, a payment page, a confirmation page, or any other page by which the client can purchase the selected timeslot). If however, the client selects a timeslot that is not available or open, the method can proceed to block 260.

At block 260, the server 101 can receive a request from the client electronic device 150a-c for an appointment with the professional that is displayed on a list of available appointments at the professional's profile 600. Similarly, the method can proceed to block 260 if the client transmits a request to the server 101 for an appointment that is designated as not open or unavailable on the list of available appointments at the professional's profile 600. If the client requests an appointment that is unavailable, not open, or not listed in the available appointment of the professional, at block 260, the server 101 can transmit a request to the professional's electronic device 175a-b. The request transmitted to the professional's electronic device 175a-b can be a request for the professional to open the appointment (that is, accept the client's suggested appointment) or reject the suggested appointment. If the professional accepts the client's suggested appointment, the method can proceed to block 265.

At block 265, the server 101 can receive a notification from the professional's electronic device 200 indicating that the professional has accepted the client's suggested appointment. The notification can include data indicating that the professional has opened up a timeslot in his or her schedule at the date and time corresponding to the client's suggested appointment. After the server 101 receives notification that the professional has accepted or opened the timeslot suggested or requested by the client, the method can proceed to block 270, as described above. At block 270, the server 101 can receive a request from the client electronic device 150a-c to purchase the newly opened timeslot. A confirmation of the purchase can be transmitted from the client electronic device 150a-c to the server 101. After the server 101 receives confirmation of the purchase of the timeslot, the method 200 can proceed to block 275.

At block 275, the server 101 can establish an appointment interface or a virtual consultation interface by which the client and the professional can conduct the virtual consultation (such as an online consultation). The appointment interface or virtual consultation interface can be a teleconference, a videoconference, a web-based teleconference, a web-based videoconference, an electronic chat room, a video chat, or any other interface by which the client and the professional can conduct a consultation remote from one another. In one embodiment, the server 101 can establish the appointment interface or virtual consultation interface a predetermined time period prior to the scheduled purchased timeslot, for example, five minutes prior, ten minutes prior, one minute prior, five seconds prior, thirty seconds prior, or any other predetermined period prior to the purchased timeslot. The predetermined time period can be set by the proprietor of the server 101, and administrator of the server, the client, the professional, or any combination thereof. When the server 101 establishes the appointment interface or the virtual consultation interface, the server 101 can transmit a notification to each of the client electronic device 150a-c and the professional electronic device 175a-b indicating that the appointment interface or virtual consultation interface is available. For example, the notification can include an access point (for example, a hyperlink, a dial-in number, or any other access point) by which the professional electronic device 175a-b and the client electronic device 150a-c can connect to the virtual consultation interface to conduct the virtual consultation. At the conclusion of the virtual consultation (for example, by the professional terminating the virtual consultation or the allotted time or duration of virtual consultation expiring), the method 200 can proceed to block 280.

At block 280, the server 101 can transmit data to the client electronic device 150a-c for displaying a review form by which the client can generate a review of the professional's performance during the virtual consultation. The review form can include a free-form text box, a rating selection from a rating scale, one or more questions including associated selectable answers, or any other similar review by which the client can evaluate and comment on the professional's performance during the virtual consultation. After the client completes the review, the completed review can be received by the server 101. The server 101 can store the review in the client review database 120. The server 101 can also sort, aggregate, and compile the data from the client's review. The server 101 can also process the client's review to extract data and correlate the data with search terms of the search terms database 110. The server 101 can also correlate or pair the client's review to one or both of the corresponding professional's data stored in the professionals database 105 and a peer performance review associated with the professional who the client's review is about. In other words, he client's review can be utilized by the server 101 for future search queries of professionals by the client or any other client accessing the virtual professionals community.

Figure 3:
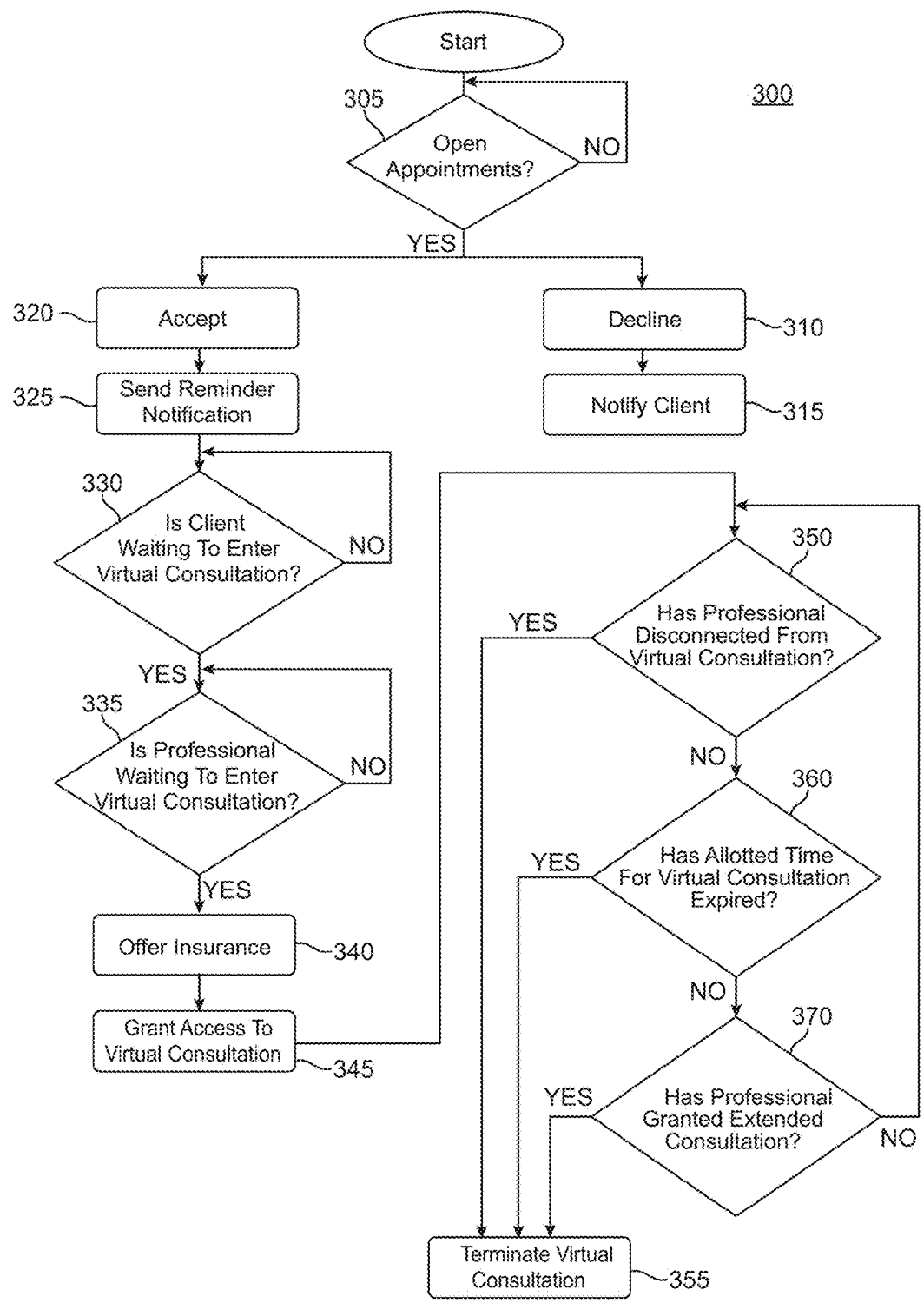
FIG. 3 is a flow chart illustrating an example method of professional's acceptance of a requested virtual consultation, in accordance with an example embodiment of the present disclosure.

FIG. 3 is a flow chart illustrating a method 300 a professional's interaction with the virtual professionals community to schedule and conduct a virtual consultation with a client. In FIG. 3, the professional is a doctor or medical professional, and the client is a patient. The method 300 illustrated in FIG. 3 starts after the client electronic device 150a-c has transmitted a request for an appointment (for example, such as at block 260 of FIG. 2). The method 300 of FIG. 3 is provided by way of example, as there are a variety of ways to carry out the method. Additionally, while the example method 300 is illustrated with a particular order of steps, those of ordinary skill in the art will appreciate that FIG. 3 and the steps illustrated therein can be executed in any order that accomplishes the technical advantages of the present disclosure and can include fewer or more steps than illustrated.

In FIG. 3, the method 300 can begin at block 305. At block 305, the server 101 can determine whether there are any open or scheduled appointments for the professional electronic device 175a-b. For example, the server 101 can review a calendar or schedule associated with the professional electronic device 175a-b and determine whether there are any scheduled appointments for the professional associated with the professional electronic device 175a-b. If there are any scheduled appointments or proposed on the professional electronic device's 175a-b calendar, a notification can be transmitted from the server 101 to the professional electronic device 175a-b. For example, a notification can be transmitted from the server 101 to the professional electronic device 175a-b that there are proposed appointments on the professional's calendar or schedule that have not yet been accepted by the professional. If there are proposed appointments on the professional's calendar or schedule, the method 300 can proceed to either block 310 or 320.

At block 310, if the server 101 receives data from the professional electronic device 175a-b indicating that the professional has declined or rejected a proposed appointment. For example, the professional can select a selectable option displayed on the professional's profile or home page to decline or reject the proposed appointment, and data indicating the rejection of the appointment can be transmitted to the server. If the server 101 receives data indicating that the professional has declined or rejected the proposed appointment, the method 300 can proceed to block 315.

At block 315, the server 101 can transmit a notification to the client electronic device 150a-c that requested the proposed appointment. The notification can notify the client that the selected professional has declined the client's proposed appointment. The client can thereby select another professional for a virtual consultation or request another appointment at a different timeslot.

If however, the server 101 receives data indicating that the professional has accepted the client's proposed appointment, the method can proceed to block 320. At block 320, the server can process the data indicating the professional has accepted the client's proposed appointment. In response, the server 101 can place an appointment on a calendar or schedule of each of the client and professional. Additionally, the server 101 can generate reminder notifications to transmit to each of the client electronic device 150a-c and the professional electronic device 175a-b. After the server 101 has processed the professional's acceptance of the proposed appointment and reminder notifications are generated, the method can proceed to block 325.

At block 325, the server 101 can send or transmit reminder notifications to each of the client electronic device 150a-c and the professional electronic device 175a-b. The server 101 can transmit the reminder notifications a predetermined time period before the scheduled appointment or consultation. The predetermined time period prior to the scheduled appointment or consultation can be five minutes prior, ten minutes prior, one minute prior, five seconds prior, thirty seconds prior, or any other predetermined period prior to the purchased timeslot. The predetermined time period can be set by the proprietor of the server 101, and administrator of the server, the client, the professional, or any combination thereof. The reminder notification can also include an access point for accessing the virtual consultation interface or the appointment interface, as discussed above in relation to FIG. 2. After the reminder notification is transmitted to each of the client electronic device 150a-c and the professional electronic device 175a-b, the method 300 can proceed to block 330.

At approximately the scheduled timeslot for the scheduled appointment, the server 101 can determine whether the client electronic device 150a-c has accessed the access point for the virtual consultation interface or the appointment interface. In FIG. 3, the client electronic device 150a-c can be placed in a waiting room GUI before being connected to the virtual consultation interface or the appointment interface. For example, in one embodiment, the client electronic device 150a-c may not enter or access the virtual consultation interface or the appointment interface until the professional enters or accesses the virtual consultation interface or the appointment interface. In other words, the professional electronic device 175a-b can control the initiation or start of the virtual consultation. If the server 101 determines that the client electronic device 150a-c has accessed the access point for the virtual consultation interface or the appointment interface and that the client electronic device 150a-c is waiting for the virtual consultation to begin, the method 300 can proceed to block 335.

At block 335, the server 101 can determine whether the professional electronic device 175a-b has accessed the access point for the virtual consultation interface or the appointment interface and is waiting to enter or begin the virtual consultation. If the server 101 determines that the professional electronic device 175a-b has accessed the access point for the virtual consultation interface or the appointment interface and is waiting to enter or begin the virtual consultation, the method can proceed to block 340.

At block 340, the server 101 can transmit data to the professional electronic device 175a-b for displaying a GUI in which a professional insurance coverage (for example, medical malpractice insurance, legal malpractice insurance, a professional liability insurance, or any other professional insurance coverage) is offered to the professional for the scheduled virtual consultation. The professional insurance coverage can be specific to the scheduled virtual consultation. That is, the professional insurance coverage can have a coverage period that expires at the termination of the virtual consultation. The amount of coverage of the professional insurance can also be specific to the scheduled virtual consultation. For example, the amount of coverage of professional insurance can be determined based on the symptoms, conditions, diseases, and problems for which the client seeks the virtual consultation. In another example, the amount of coverage of professional insurance can also be based on or can instead be based on one or more of a specialty of the professional, a peer review rating of the professional, and a client review rating of the professional. In response to transmitting data for offering the professional insurance coverage to the professional, the server 101 can receive data indicative of the professional's acceptance or rejection of the professional insurance coverage. If the professional accepts the professional insurance coverage, the professional insurance coverage can be applied to the virtual consultation. If the professional rejects the professional insurance coverage, the professional insurance coverage will not be applied to the virtual consultation. After the server 101 receives data indicating the professional's acceptance or rejection of the professional insurance coverage, the method 300 can proceed to block 345.

At block 345, the server 101 can grant access to the virtual consultation (for example, a GUI illustrating a virtual doctor's office or a virtual professional's office) to each of the client electronic device 150a-c and the professional electronic device 175a-b. As discussed above, in relation to FIG. 2, the virtual consultation can be a teleconference, a videoconference, a web-based teleconference, a web-based videoconference, an electronic chat room, a video chat, or any other interface by which the client and the professional can conduct a consultation remote from one another. After the client and the professional have entered the virtual consultation, the method can proceed to block 350 to determine whether the virtual consultation has terminated.

At block 350, the server 101 can determine whether the professional electronic device 175a-b has disconnected from the virtual consultation. For example, the server 101 can determine whether the professional has selected a "terminate" or "end session" option to terminate or end the virtual consultation. For example, by entering an input at the professional electronic device 175a-b, inputting a gaze command, a motion command, a voice command, or any other input representing a selection. In another example, the server 101 can determine whether the professional has inactively terminated or ended the virtual consultation. For example, the professional can inactively terminate or end the virtual consultation by exiting or closing a browser by which the professional accessed the virtual consultation, by losing a network connection to the virtual consultation interface or the appointment interface, or otherwise disconnecting from the virtual consultation interface. If the server 101 determines that the professional electronic device 175*a-b* has disconnected from the virtual consultation interface, the method 300 can proceed to block 355.

At block 355, the server 101 can terminate the virtual consultation. For example, the server 101 can terminate the virtual consultation even if the client electronic device 150*a-c* has not actively or inactively terminated the client electronic device's 150*a-c* connection to the virtual consultation.

If the server 101 determines that the professional electronic device 175*a-b* has not disconnected from the virtual consultation interface, the method 300 can proceed to block 360. At block 360, the server 101 can determine whether an allotted time for the virtual consultation has expired. For example, when the professional electronic device 175*a-b* enters the virtual consultation, the virtual consultation can begin, thereby starting a clock associated with the virtual consultation. For example, if the virtual consultation has a predetermined allotted duration of twenty minutes, thirty minutes, one hour, or any other predetermined allotted duration, the clock can count down or count up until the predetermined allotted duration has been met, thereby notifying the client and the professional that the virtual consultation. When the allotted time for the virtual consultation has been met or has expired, the method can proceed to block 355, and the virtual consultation can be terminated, as described above. If however, the server 101 determines that the allotted time for the virtual consultation has not expired, the method can proceed to block 365.

At block 365, the server 101 can maintain the virtual consultation, thereby permitting the client and professional to continue conducting the virtual consultation. The server 101 can also determine whether the professional electronic device 175*a-b* has granted an extension of time for the virtual consultation. For example, the professional electronic device 175*a-b* can actively extend the duration of the virtual consultation, for example, by selecting or entering a command to extend the duration for the virtual consultation. In one example, the professional electronic device 175*a-b* can extend the duration of the virtual consultation by one minute, five minutes, ten minutes, twenty minutes, or any other duration. If the server 101 determines that the professional has granted an extension of time for the duration of the virtual consultation, the server 101 can maintain the establishment of the virtual consultation interface, thereby allowing the client and professional to continue conducting their virtual consultation. If however, the server 101 determines that the professional has not granted an extension of time, the method can proceed to block 355, and the virtual consultation can be terminated, as discussed above.

In FIG. 3, it will be appreciated that the duration of the virtual consultation is controlled or dictated by the connection of the professional electronic device 175*a-b* to the virtual consultation interface. That is, the professional can control the start and stop of the virtual consultation. The client is simply a participant of the virtual consultation but does not have control over when the virtual consultation begins or ends.

The disclosure now turns to FIGS. 4-21 which illustrate a specific example of searching for a professional of a virtual professionals community in accordance with the present disclosure, booking an appointment for a virtual consultation with a selected professional, having the professional confirm the selected appointment, and conducting the virtual consolation.

Figure 4:
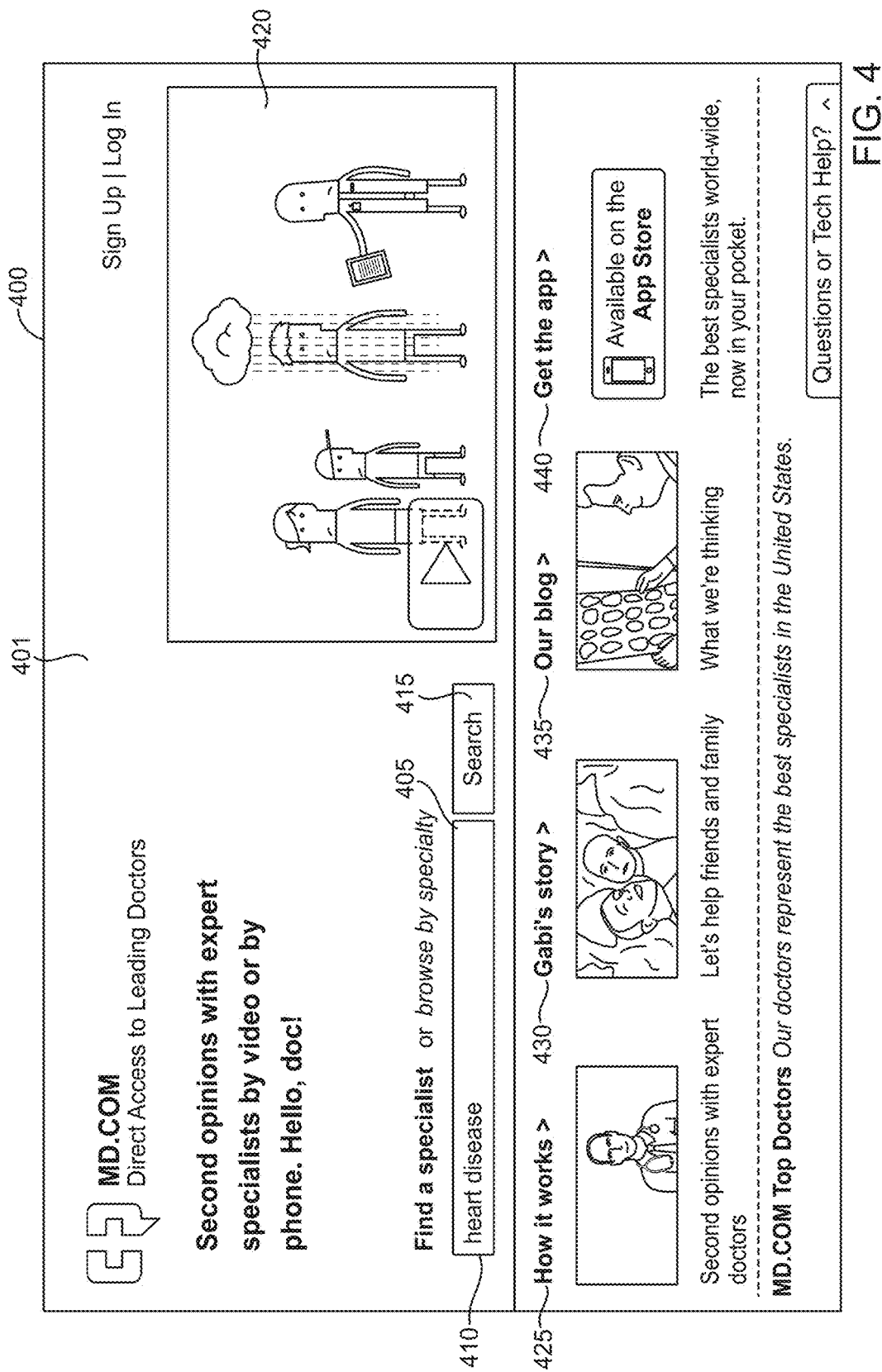

FIG. 4 illustrates a graphical user interface (GUI) 400 that can be displayed on a display screen of a client's electronic device 150*a-c*. In FIG. 4, the GUI 400 displays a home page 401 of the virtual professionals community. The home page 401 can be the same for any client, potential client, professional, or potential professional who may visit he virtual professionals community. In other embodiments, where the client or the professional is already a member of the virtual professionals community, the home page 401 can be different from that illustrated in FIG. 4. For example, the home page 401 can be customized based on the client or professional visiting the virtual professionals community. In one example, the customized home page can be displayed after the client or professional enters or inputs his or her user credentials at the home page 401 (for example, by logging in an entering a user name and password or other user credentials).

Also illustrated in FIG. 4, the GUI 401 can include a video 420. The video 420 can be an advertisement associated with the virtual professionals community, an advertiser affiliated with the virtual professionals community, or a professional of the virtual professionals community. The video 420 can also be a demonstration video or an instructional video demonstrating how to conduct a search for a professional, how to conduct a virtual consultation, or any other type of instruction that a client may need to learn how to interact with GUI 400 of the virtual professionals community.

In FIG. 4, the home page 401 can include a plurality of links 425, 430, 435, 440 or sections associated with the virtual professionals community. For example, the home page 401 can include a How it Works link 425. The How it Works links 425, when selected, clicked, or otherwise designated, can display another page of content containing information or instructions associated with search for professionals within the virtual professionals community and booking or scheduling virtual consultations with the professionals. The home page 401 can also include a client's story link 430. The page of content can be a webpage, a video, audio, a slideshow, and animation, or any other page of content. The client's story link 430, when selected, clicked, or otherwise designated, can display a page of content containing information associated with a current or past client's story of his or her experience with the virtual professionals community. For example, the client's story link 430 can display a video the client's story. In other embodiments, the client's story link 430 can be a webpage, a video, audio, a slideshow, and animation, or any other page of content which provides information associated with a client's story regarding his or her experience with the virtual professionals community. The home page 401 can include a blog link 435. The blog link 435 can display a blog, a message board, a social media message board, or any other posting by which professionals and clients of the professionals community can post messages and notifications. In other embodiments, the blog link 435 can display a blog associated with one or more developers or administrators of the virtual professionals community regarding. For example, such blog can include updates to, new features, and other information associated with the virtual professionals community system 100. In still other embodiments, the blog link 412 can display a blog of a featured professional, selected by the server 101 of the virtual professionals community system 100. For example, the featured professional can be randomly selected or based on a selection criteria. For example, the featured professional can be selected based on a recent client review, a recent peer performance review, a recency of joining the virtual professionals community, a number of virtual consultations conducted, a number of client reviews, a number of peer performance reviews, or any other type of selection criteria by which a professional can be designated and identified as a featured professional. Also in FIG. 4, the home page 401 can include a Get App link 440. The Get App link 440 can display applications or features associated with the virtual professionals community (for example, the GUI 400) that clients, future clients, professionals, and future professionals can download. In one example, the Get App link 400 can display a page of content having links for downloading a mobile application, a smartphone application, an electronic pad application, software updates, or any other type of downloadable information associated with the virtual professional networks. For example, the Get App link 400 can include a link for downloading a mobile application containing a mobile version of the GUI 400 that can be displayed on a mobile electronic device.

Also illustrated in FIG. 4, the home page 401 can include a search field 405. The search field 405 can be a text-entry field by which clients can enter a search query 410. For example, clients can enter search terms or search criteria in the search field 405. Although not shown, the search field 405 can also include a link to a predetermined or pre-generated list of search criteria form which a client can formulate a search query, as described above in relation to FIG. 2. In other embodiments, the search field 405 can include a pull-down list, a pull-down menu, a cascading menu or any other type of menu form which a client can generate a search query. In FIG. 4, a client has entered a search query 410 of the search terms "heart disease" in the search field 405. In FIG. 4, a search button 415 can be provided to submit the search query 410 entered in the search field 405 to one or more servers 101 of the virtual professionals community. In other embodiments, the search query 410 can be transmitted without the selection of the search 410. In still other embodiments, a search completion list (for example, suggested search queries or suggested search terms) can be display in the search field 405 or in a search completion list (not shown) adjacent the search field 405. The search completion list can be generated as the client types the search query 410 in the search field 405. For example, the search completion list can be generated and updated each time the user enters, modifies, or deletes characters from the search field 405. After the client submits or transmits the search query 410 to the server 101 of the virtual professionals community, the server 101 can execute a search of one or more of the professionals database 105, a search terms database 110, a peer review database 115, and a client review database 120 to identify or determine professional data to suggest to the client.

Figure 5:
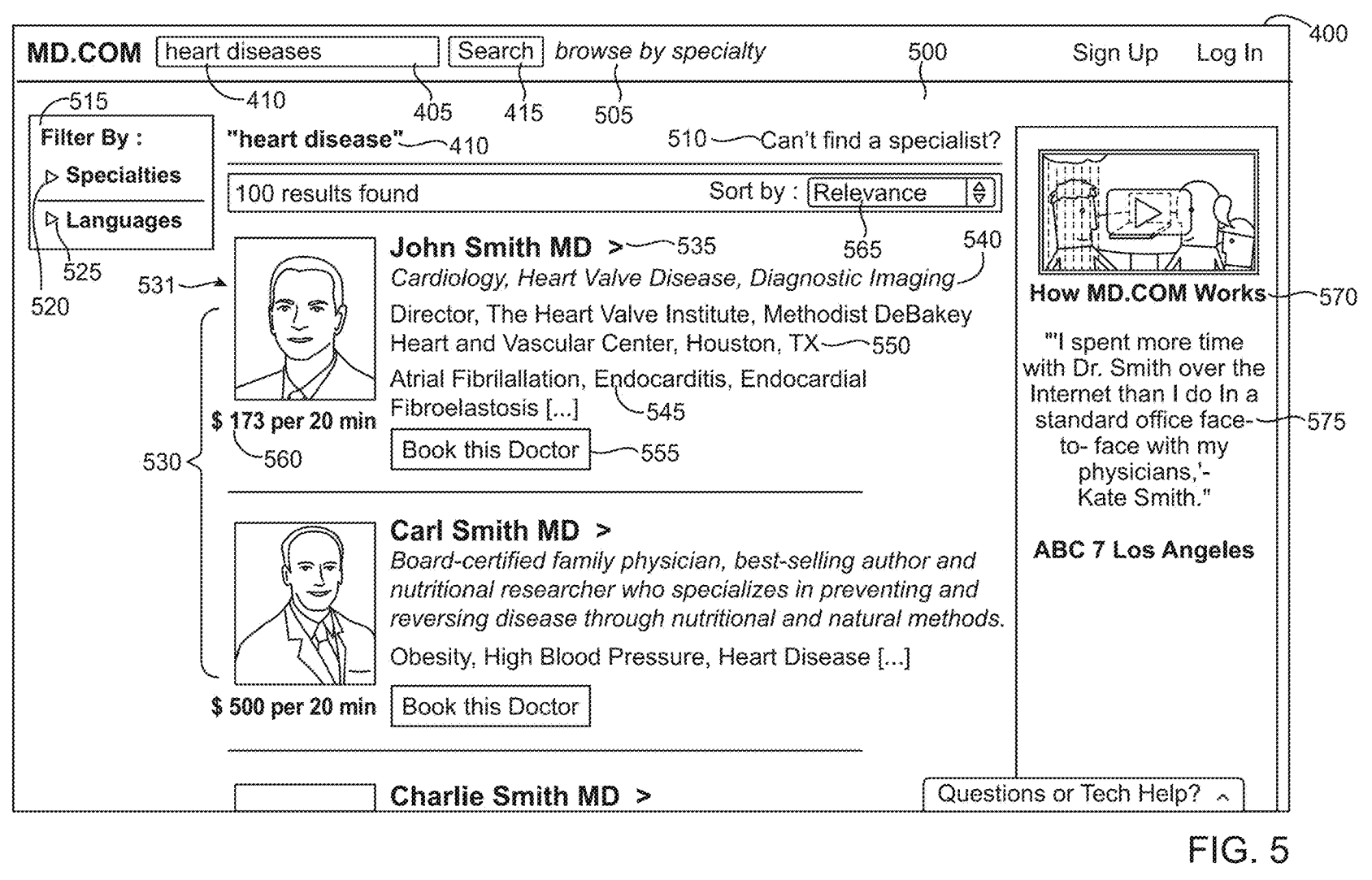

In FIG. 5, the server 101 has identified professional data to suggest to the client. FIG. 5 illustrates search results page 500 including a list or report 530 of suggested or relevant professional data 531 matching at least some of the search criteria or search terms of the client's search query 410. The professional data corresponding to suggested or relevant professionals can be identified or determined utilizing the process as described in relation to FIG. 2. In FIG. 5, the report 530 includes one hundred (100) relevant professionals 531 matching at least some of the search criteria of the client's search query 510. Those of ordinary skill in the art will appreciate that the fewer or more relevant professionals 531 matching the client's search query 510. In other embodiments, the number of returned or suggested relevant professionals 531 can be user-defined, can be determined based on the size of the display screen of the client's electronic device 150a-c, can be determined based on a resolution the display screen of the client's electronic device 150a-c, can be determined based on a bandwidth associated with one or both of client's electronic device 150a-c and the server 101. As illustrated in FIG. 5, the suggested relevant professionals 531 can include the names of summaries 535 of the suggested relevant professionals 531. For example, the summaries 535 can include the specialties of the professional 540 (for example, cardiology, heart valve disease, diagnostic imaging), a title and place of work 550 (for example, the hospital at which the suggested relevant professional works), and a list of symptoms, diseases, conditions, or problems 545 the suggested relevant professional treats. The report 530 can also include a rate 560, cost, or price for conducting a virtual consultation with the respective suggested relevant professional 531. For example, in FIG. 5, the rate associated with the first suggested professional is $173 per 20 minutes. In other words, the cost of a 20 minute virtual consultation with the suggested professional is $173. The rate 560 can be determined by the professional or can be determined or set by the server 101. If the server 101 determines the rate, the rate can based on one or more of the specialty 540 of the professional, a level of experience of the professional, years of experience of the professional, prior rates of the professional, peer performance reviews, client reviews, or any other factors for determining a rate 560. Also illustrated in FIG. 5, the report 530 can include a selectable option 555 (for example, "Book this Doctor" button) for booking an appointment or scheduling an appointment with the corresponding suggested professional. Selection of the user selectable option 555 can display an appointment page, a pop-up window, or any other GUI by which the client can schedule a virtual consultation with the corresponding suggested professional, as will be discussed in further detail below in relation to FIG. 9.

In FIG. 5, the suggested relevant professionals 531 can be default sorted or ranked, as discussed above, based at least in part on a relevancy score and a peer performance review rating. In FIG. 5, the client can re-order or re-sort the order of the suggested relevant professionals 531 in the report 530 by selecting a sorting option 565. In FIG. 5, the sorting option 565 can be a drop down menu, a radio button, a dialogue button, or any other user-selectable option. For example, the client can re-order or re-sort the order of the suggested relevant professionals 531 in the report 530 based on rates, based on specialties, based only on peer performance review ratings, based only on client review ratings, based only on a relevancy score, or any other sorting criteria as discussed above.

Also illustrated in FIG. 5, the search results page 500 can include a concierge link 510 (for example, a "Can't find a specialist?" link 510) by which a client can consult with a concierge to formulate a search query, refine his or her search query 410, or otherwise receive assistance in finding an appropriate professional for evaluating or consulting with the client regarding the client's search query 410.

The search results page 500 can also include a filter option 515. The filter option 515 can allow the client to filter the suggested professionals 531 provided in the report 530. For example, the client can filter the suggested professionals 531 provided in the report 530 based on specialties 520, languages spoken 525, genders, educational credentials, rates, or any other filtering criteria as discussed above.

Alternatively, if the client desires to change his or her search query, a search bar including the search field 405 can be provided with the search results page 500. The client can refine, modify, or change his or her search query using the search field 405. In another embodiment, the client can select a "browse by specialty" option 505 by which the client can formulate a search using a predetermined or pre-generated list of search terms or categories for searching for suggested professionals. For example, the "browse by specialty" option 505 can direct the client to a page of content that includes cascading menus or a plurality of categories and search terms that the client can select or designate to search for suggested professionals.

Also in FIG. 5, the search results page 500 can optionally include a video 570 of a prior client's experience with conducting virtual consultations in the virtual professionals community. Also illustrated in FIG. 5, the search results page 500 can include text 575 associated with the video. For example, the test 575 can include a quote from a prior client regarding his or her experience with conducting virtual consultations in the virtual professionals community. In FIG. 5, the video 570 and associated text 575 can be displayed adjacent the search results report 530, but can also be placed elsewhere on the search results page 500.

In FIG. 5, the client can select the first suggested professional 531 of the search report 530. As discussed above, the first suggested professional 531 can be the suggested professional 531 that has the highest relevancy score and the highest peer performance review rating. In FIG. 5, the client can select the first suggested professional 531 by selecting, clicking, or otherwise designating the name of the first suggested professional 531 or selecting, clicking, or otherwise designating the "Book this doctor" button 555. In response to the selection of the first suggested professional 531, the server 101 can transmit data to the client electronic device 150a-c to display a professional information page 600 (illustrated in FIG. 6) associated with the selected first suggested professional 531.

Figure 6:
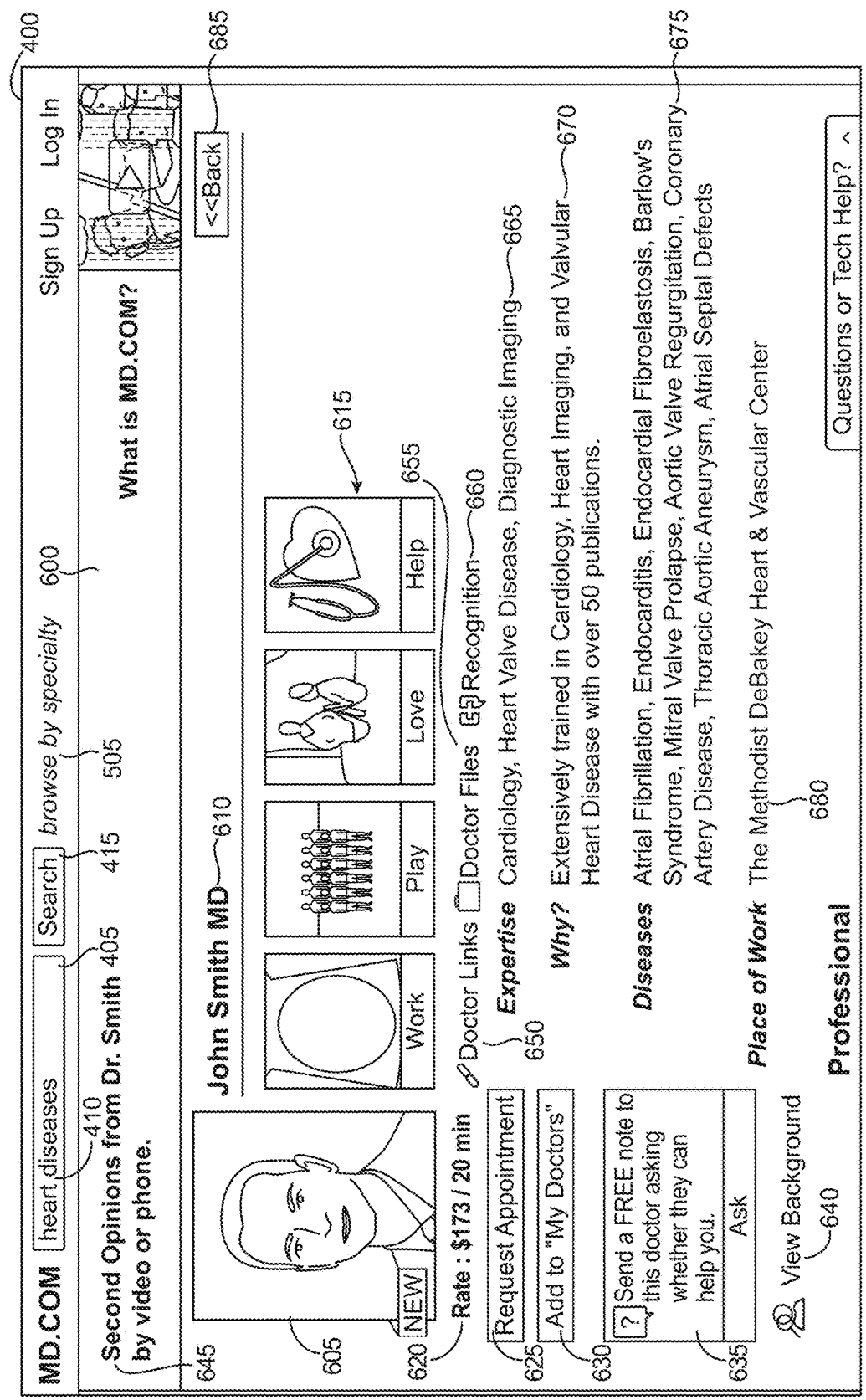

FIG. 6 illustrates the doctor home page 600 associated with the selected first suggested professional 531 of FIG. 5. In FIG. 6, the professional information page 600 can include a plurality of information associated with the selected first suggested professional 531. In FIG. 6, the professional information page 600 includes a name 610 of the suggested professional 531, a picture 605 of the suggested professional 610, a rate 620 for conducting a virtual consultation with the suggested professional 610. The professional information page 600 can also include a list of interests 615 associated with the suggested professional (for example, work, paly, love, and help) or any other personal interests of the suggested professional 610. The professional information page 600 can also include detailed information 665, 670, 675 associated with the practice or specialties of the professional 610. For example, in FIG. 6, the detailed information can include expertise information 665 (such as specialties of the professional). The detailed information can also include a reason 670 a client should select the professional 610 (which can be generated by the professional, a peer of the professional, a prior client of the professional, a former professor of the professional, a colleague of the professional. or any other person or entity associated with the professional). The detailed information can further include a list of diseases 675 which the professional treats, diagnosis, or evaluates. In other embodiments, the list can include a list of problems, symptoms, or other issues which are addressed or evaluated by the professional. The detailed information can also include a place of work 680 of the professional. For example, the place of work 680 can include the current employer or the current institution of the professional. In FIG. 6, the place of work can be the hospital at which the professional works.

Also illustrated in FIG. 6, the professional information page 600 can include a Request Appointment option 625 for scheduling, booking, or requesting an appointment with the professional. Details regarding a selection of the Request Appointment option 625 will be discussed in relation to FIG. 9 below.

The professional information page 600 can include an Add to "My Doctors" option 630. The Add to "My Doctors" option 630 can be selected by the client to save or otherwise mark the professional information page 600. For example, the Add to "My Doctors" option 630 can be selected to mark or bookmark the professional information page 600 as a page of interest or a page the client would like to re-visit. That is, if the client approves of the credentials and detailed information about the professional but is not certain that the client would like to book an appointment with the professional, or if the client desires to review other professionals' information pages before booking an appointment with the professional associated with the current professional information page 600, the client can select the Add to "My Doctors" option 630 to save the professional information page 600 in a "My Doctors" list, dataset or other repository for saved or marked professional information pages.

FIG. 6 also illustrates a Send a Free Note option 635. The Send a Free note option 635 can be selected by the client to transmit a yes or no question to the professional of the professional information page 600. The question can be transmitted the professional electronic device 175a-b of the professional so that the professional can answer the client's question to assist the client in determining whether the client should book or schedule a virtual consultation with the professional of the professional information 600. Further details as to the Send a Free Note option 635 will be described in relation to FIGS. 8 and 14.

Also illustrated in FIG. 6, the professional information page 600 can include a view background option 640. For example, selection of the background option 640 can retrieve a background check of the professional of the professional information page 600.

In FIG. 6, the professional information page 600 can include plurality of tabs 650, 655, 660. The tabs can include a doctor links tab 650 comprising one or more links the professional suggests clients or other professionals to visit. The tabs can also include a doctor files tab 655 comprising one or more documents uploaded by the professional and shared by the professional to clients and other professionals visiting the professionals information page 600. For example, the doctor files tab 655 can include publications written by the professional, publications written about the professional, videos or other media files presented by the professional or about the professional, or any other document or files the professional desires to share with the virtual professionals community. Also shown in FIG. 6, the tabs can include a recognition tab 660. The recognition tab 660 can comprise any recognitions or award the professional receives. The recognition tab 660 can also include the peer performance reviews and the client reviews about the professional. When the recognition tab 660 is selected, the professional information page 600 can be updated to display the information contained in the recognition tab 660 as illustrated in FIG. 7.

Also illustrated in FIG. 6 is a back button 685 by which the user can return to the report 530 or list of suggested professionals meeting search criteria associated with the client's search query 410.

Figure 7:
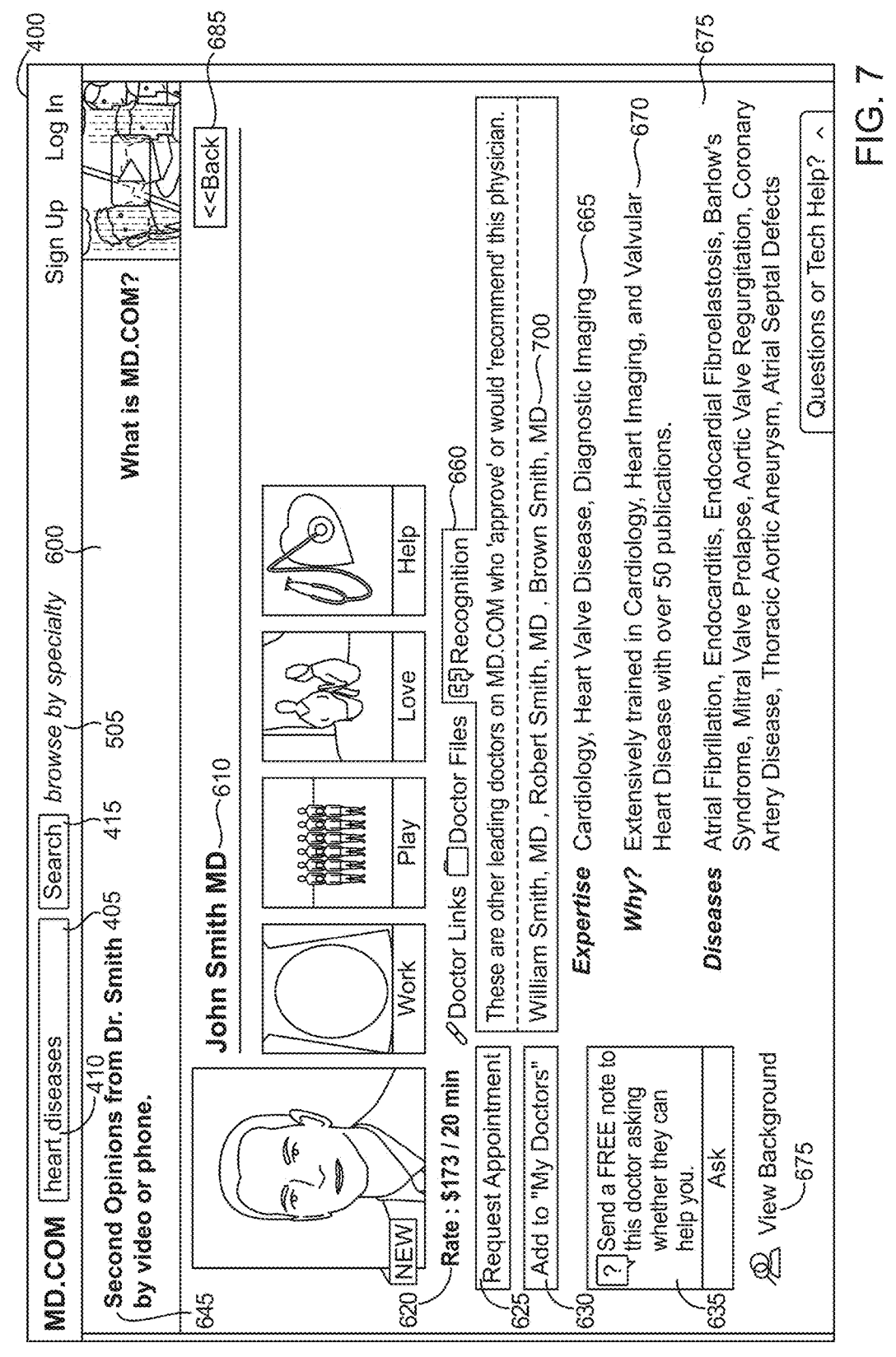

In FIG. 7, the recognition tab 660 is selected. In response to the selection of the recognition tab 660, information or content 700 associated with the tab 660 can be overlaid on or displayed adjacent to the detailed information of the professional information page 600. In other embodiments, selection of the recognition tab 660 can display a new page of content containing the information or content 700 associated with the tab 660. In FIG. 7, the information associated with the recognition tab 660 can include a list of peer professionals who have approved or recommended the professional associated with the professional information page 600, a summary of or the actual peer performance reviews and rankings, a summary of or client reviews and rankings, a list of awards or recognitions received by the professional, or any other similar information by which a client can make an informed decision as to whether to schedule a virtual consultation with the professional of the professional information page 600.

Figure 8:
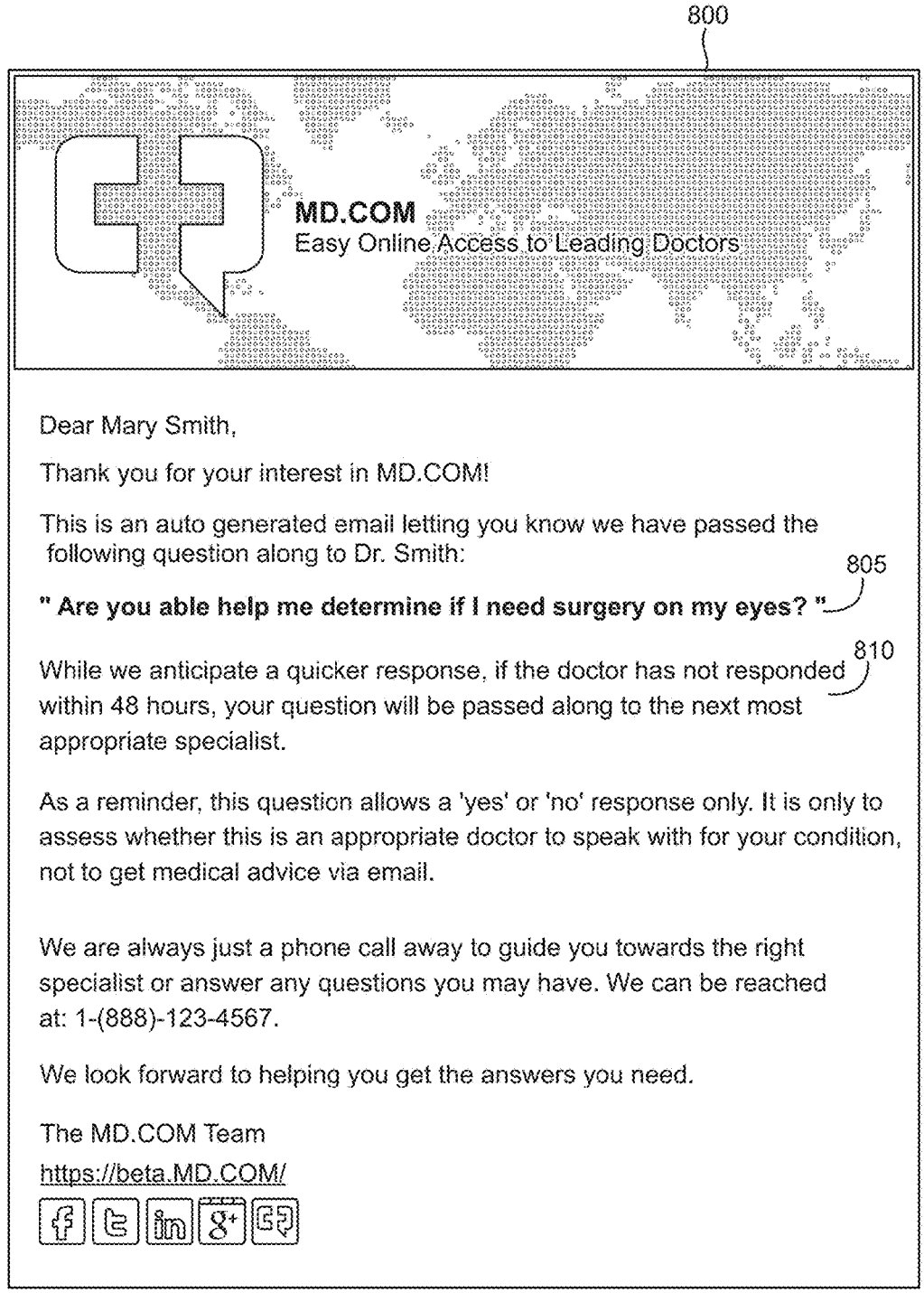

If the Send a Free note option 635 shown in FIG. 6 or 7 is selected, the client can transmit a yes or no question to the selected professional of the professional information page 600, as illustrated in FIG. 8. The yes or no question can be answered by the professional to assist the client in determining if the professional is the appropriate professional for consulting with the client regarding the client's problems, issues, disease, or symptoms. FIG. 8 illustrates a confirmation 800 that the note has been sent to the professional. Specifically, in FIG. 8, the confirmation 800 identifies the yes or no question 805 asked by the client. In FIG. 8, the question 805 is "Are you able to help me determine if I need surgery on my eyes?." Such yes or no question allows the client to determine whether the suggested professional is the appropriate professional for consulting with the client regarding the client's problems, issues, disease, or symptoms. As will be described in further detail below in relation to FIG. 14, if the professional responds to the question 805 in the affirmative (for example, by answering "yes"), a notification can be transmitted to the client indicating so. If however the professional responds to the question 805 in the negative (for example, by answering "no"), a notification can be transmitted to the client indicating so, and the question can be sent to the next suggested professional listed in the search results report 530. The next-listed suggested professional (that is, the suggested professional listed below the professional who responded in the negative) will receive the question 805 as the next-listed suggested professional has been determined as being the next most-qualified or relevant professional to consult with the client regarding the client's problems, issues, disease, or symptoms. In at least one embodiment, the confirmation 800 can include text indicating that if the doctor has not responded with a predetermined period of time (predetermined by the server 101, the client, the professional, an administrator of the virtual professionals community, or any other person or entity associated with the virtual professionals community), the question 805 will be passed along or transmitted to the next-listed or next most appropriate professional.

If the client receives a notification that the professional has answered his or her question 805 in the affirmative, the client can select the "Request Appointment" option 625 provided on the professional information page 600. In response to the selection of the "Request Appointment" option 625, a Book Doctor page 925 can be displayed in a the client account GUI 900 of the client electronic device 150a-c.

The client account GUI 900 can include options for a My Health tab 905, a My Doctors tab 910, a shopping cart 915, and an accounts setting menu 920. The My Health tab 905 can be selected to display the prior diagnoses, symptoms, biographical information, and other health information associated with the client. The My Doctors tab 910 can display the professionals or doctors with whom the client previously consulted, professionals or doctors saved by the client during a search query, favor professionals or doctors designated by the client, or any other information associated with doctors designated by the client. The accounts setting menu 920 can include information (such as financial information, contact information, user credentials, display preferences, search preferences, ranking preferences, or any other information associated with the client's account. The shopping cart 915 can display a history of virtual consultations conducted by and purchased by the client. The shopping cart 915 can include any pending consultations that the client has indicated for purchasing. The shopping cart 915 can also include the Book Doctor page 925. In response to the selection of the "Request Appointment" option 625, the client account GUI 900 can be displayed to show book Doctor page 925 of the shopping cart 915 of the client.

In FIG. 9, the Book Doctor page 925 identifies the name 930 of the doctor or professional with whom the client desires to purchase or book a virtual consultation. As shown in FIG. 9, the Book Doctor page 925 can include a schedule or calendar listing the available appointments for the doctor or professional. In FIG. 9, the Book Doctor page 925 can include the current time 935 and a change button 940. The change button 940 can be selected to change a time zone for the current time 935 or any other setting associated with the current time. FIG. 9 illustrates a calendar 945 listing the available appointments or timeslots for a virtual consultation with the doctor John Smith MD. The calendar 945 can be modified by changing a month and year option 946, thereby allowing the client to view future appointments with the professional or doctor. In FIG. 9, the calendar 945 identifies dates of past appointments or unavailable appointments 949 in a first color and dates of available or open appointments 947 in a second color. The dates indicated as being available can be selected by the client. The client can further narrow the available timeslots by identifying or selecting a preferred time 977 for the virtual consultation. For example, in FIG. 9, the date Apr. 13, 2012 is selected from the calendar 945. In response to the selection, the timeslots or appointments available for the selected date 950 (Apr. 13, 2012) are displayed on the Book Doctor page 925. For example, in FIG. 9, the available appointments 955 can be listed adjacent to the displayed selected date 950. In FIG. 9, the available three available appointments 955 are displayed. Each of the available appointments 955 has a corresponding Add to Cart option 960. While only three available appointments as shown, fewer or more available appointments can be displayed depending on the professional's availability for the selected date 950. In FIG. 9, the client has selected the 1:00 am timeslot 955, and the corresponding Add to Cart Option has been changed to a Remove from Cart option 965, thereby indicating that the client has a pending purchase for the 1:00 am timeslot 955 in his or her shopping cart 915. In FIG. 9, the times shown in the timeslots 955 are displayed in the time zone designated by the client's electronic device.

However, the client can select the change button 940 to display the timeslots 955 in the time zone of the professional. Also shown in FIG. 9, the client can select one or more timeslots 955 for the selected date 950. In other embodiments, the client can select a further date. After the client has finished selecting timeslots for purchase, the client can select a Check Out option 970 to proceed with purchasing the selected timeslot 955. While FIG. 9 illustrates that a client has selected a timeslot 955 designated by the professional (for example, John Smith MD) as being available for a virtual consultation, the client can select a timeslot 955 that is not designated as being available.

For example, in FIG. 9, the client can select a Send Request option 985. Selecting the Send Request option 985 can send a request to the professional to open a future timeslot for a future timeslot that is not shown as the professional being unavailable. The professional can respond to the client's request by declining the request or confirming the request. If the professional confirms the request, a timeslot corresponding to the client's request can be opened for selection by the client. In other embodiments, the confirmation by the professional can automatically add the requested timeslot to the client's shopping cart 915.

Another feature illustrated in FIG. 9 is an option for allowing the client to schedule or book recurring appointments 980 with the professional. For example, the client can book future appointments with the professional at the same time (for example, 1:00 am) for the next three weeks on the same day, for the next three days, or any other periodic or recurring period.

In FIG. 9, when the client selects the Check Out option 970, a checkout page (not shown) can be displayed to the client. At the checkout page, the client can enter his or her financial information or billing information that the client desires to use for purchasing his or her selected timeslots. After the client submits his or her billing information, a shopping cart page 1005 can be displayed at the GUI 400 of the client electronic device 150*a-c*, as illustrated in FIG. 10.

Figure 10:
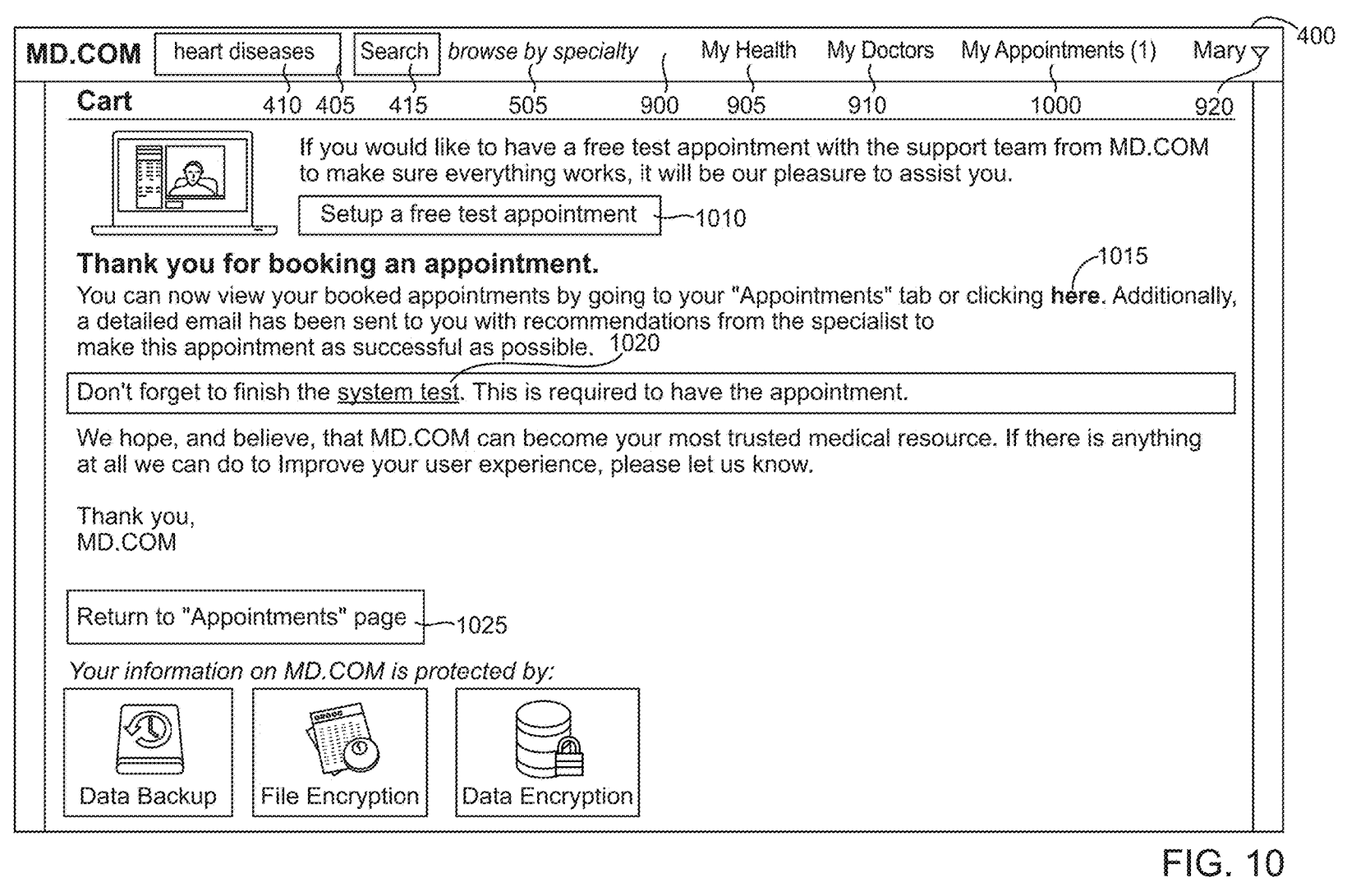

In FIG. 10, the shopping cart page 1005 can display a confirmation that the client has purchased an appointment. The confirmation can include a user selectable option for setting up a free test appointment 1010 to ensure that the client's electronic device 150*a-c* is configured to conduct a virtual consultation. The confirmation can also include a link 1015 or a button 1025 by which the client can view pending appointments. For example, the link 1015 or button 1025 can return the user to an Appointments page comprising a history of the client's purchased appointments. For example, the Appointments page can include pending appointments, previously purchased appointments, previously conducted virtual consultations, or any other history of appointments for the client.

Figure 11:
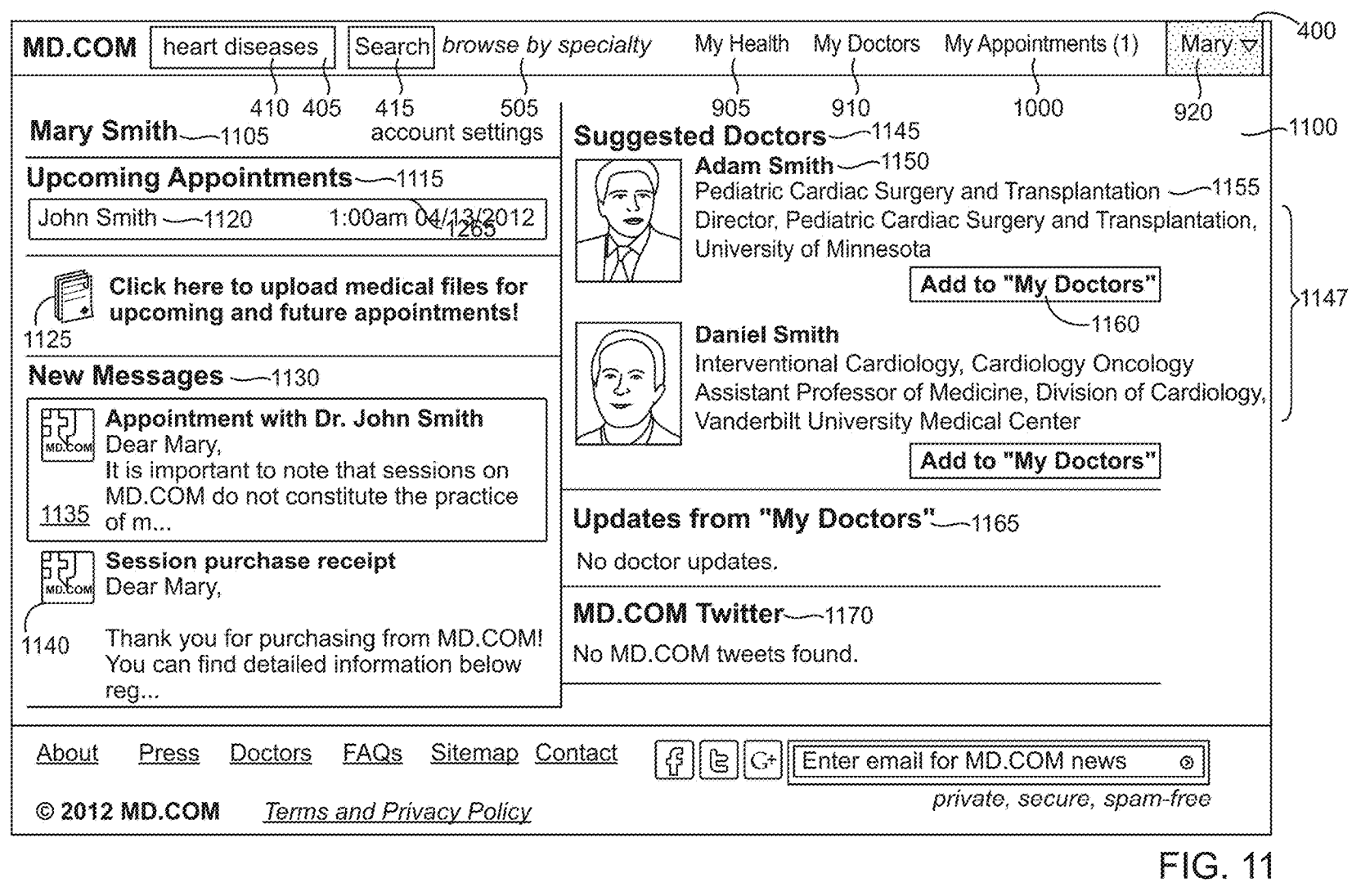

FIG. 11 illustrates a client home page 1100. In FIG. 11, the client home page 1100 includes a name 1105 of the client. The client home page 1110 can also include an Upcoming Appointments section 1115 that includes any pending appointments 1120 for the client. For example, in FIG. 11, the Upcoming Appointments page 1115 can include the appointment with John Smith MD purchased in FIG. 10. The client home page 1100 can also include a Message Inbox 1130 that displays any new messages sent to the client. For example, the Message Inbox 1130 illustrated in FIG. 11 includes a confirmation email 1135 from the professional with whom the client purchased an appointment. Specifically, in FIG. 11, confirmation email 1135 is from Dr. John Smith MD with whom the client purchased an appointment. Also illustrated in FIG. 11, the Message Inbox 1130 includes a receipt email 1140. The receipt email 1140 can be a receipt for the recent appointment purchase illustrated in FIG. 10.

The client home page 1100 can include a Suggested Doctors section 1145. The Suggested Doctors section 1145 can include at least a partial list of professionals (for example, doctors) that the server 101 of the virtual professionals network has determined as being of interest the client. For example, the list of suggested professionals can be determined based on one or more of doctors saved in the My Doctors tab 910 of the client's account, professionals with whom the client has pending or past appointments, professionals who have sent messages to the client, prior search queries, prior browsing of professionals, or any other information from which the virtual professionals network can determine whether a professional would be of interest to the client.

Also illustrated in FIG. 11, the client home page 1100 can include an "Updates from My Doctors" section 1165. The "Updates from My Doctors" section 1165 can include any messages, social networking messages (such as Twitter™ messages, Facebook™ updates, or similar social network messages associated with the virtual professionals community) sent by a professional in the client's My Doctors tab 910 or a professional that the client has designated to follow.

The client home page 1100 can further include a Twitter™ feed or any other social network distribution board 1170 or list associated with the proprietor(s), developer(s), and/or administrator(s) of the virtual professionals community. For example, the social network distribution board 1170 can display notifications or messages regarding software updates, news, or any other notifications that the proprietor(s), developer(s), and/or administrator(s) of the virtual professionals community have sent to one or both of clients and professionals of the virtual professionals community.

Figure 12:
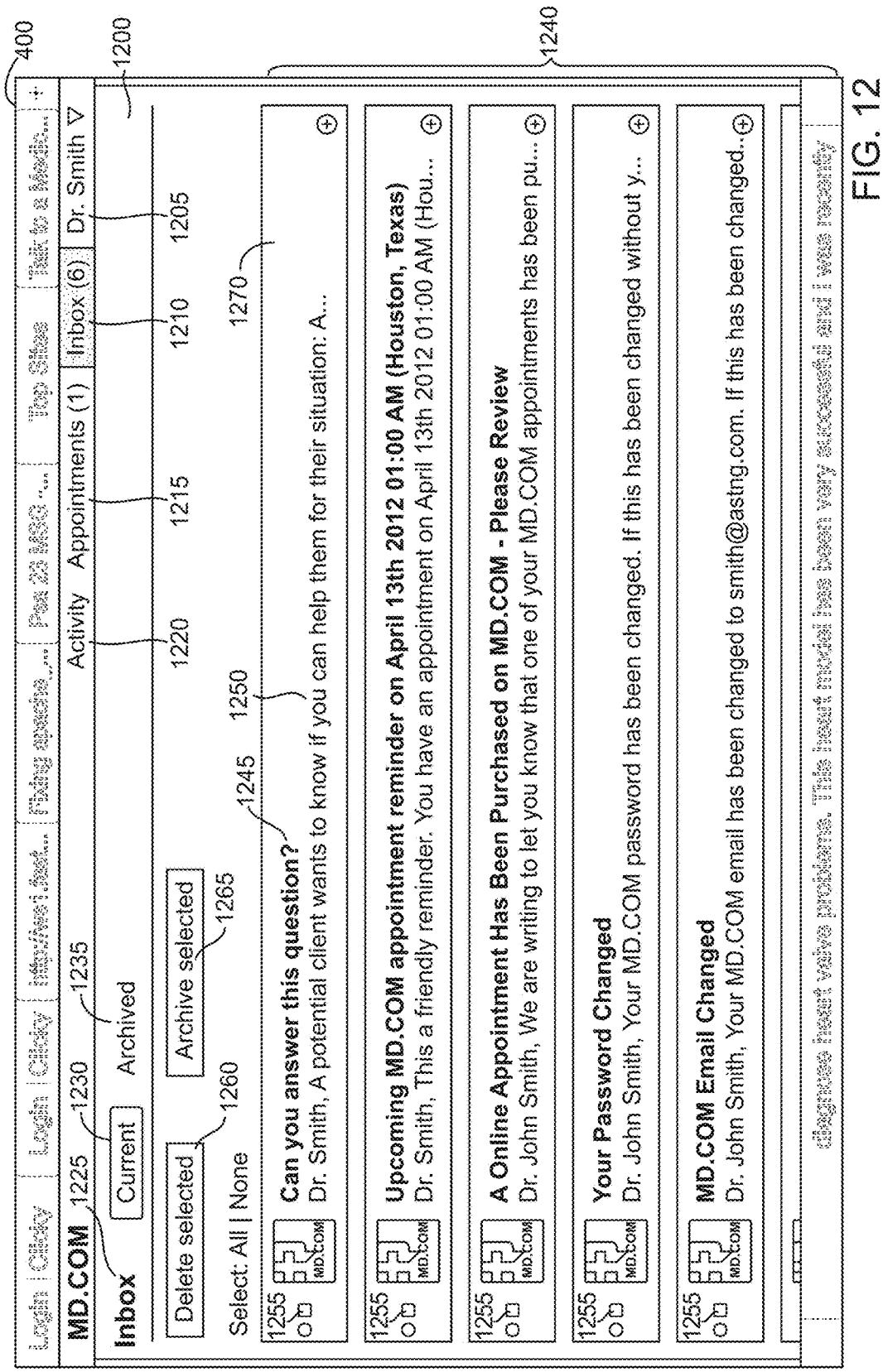

FIG. 12 illustrates a Message Inbox 1225 for a professional's home page 1200. The professional's home page 1200 can include tabs including an Activity tab 1220, an Appointments tab 1215, an Inbox tab 1210, and an account settings tab 1205. The accounts setting tab 1205 can be similar to the client's account setting tab 920 as described above. The Appointments tab 1215 can be selected to display a history of Appointments (such as past appointments, future appointments, pending appointments, or a combination thereof) that the professional has conducted or will conduct. The Activity tab 1220 can be selected to display a history of the professional's activity or interactions with the virtual professionals community. For example, the activity can include any social networking messages transmitted by the professional to his or her social network, publications, news, recognitions, completed appointments, or any other activity or interaction with the virtual professionals community.

In FIG. 12, the Inbox tab 1210 has been selected to display the Message Inbox 1225 of the professional. As illustrated in FIG. 12, the Message inbox 1225 can sort the messages therein by current messages (displayable upon selection of the current messages option 1230) and archived messages (displayable upon selection of the archived messages option 1235). In FIG. 12, the Current Messages option 1230 has been selected, and the current messages 1240 for the professional are displayed Each of the current messages 1240 includes a selectable option 1255 (for example, a dialogue button, a checkbox, or any other selectable option). The selectable option 1255 is provided to identify the corresponding message 1240 for deletion (actionable or executable upon selection of the Delete Selected option 1260) or for archiving (actionable or executable upon selection of the Archive Selected option 1265).

In FIG. 12, the Message Inbox 1225 can display a portion of the message 1240. For example, in FIG. 12, a subject line 1245, and a portion 1250 of the body of text of the message 1240 can be displayed. Fewer or more information associated with the message 1240 can also be displayed. For example, a sender, a time and date of receipt, or any other information. In FIG. 12, the Message Inbox 1225 includes a Question message 1270 corresponding to the question sent by the client in FIG. 8. Upon selection of the Question message 1270, the Question message 1270 can be expanded in the Message Inbox 1225 (shown in FIG. 13) or a new window or page can be displayed that includes the Question message 1270.

Figure 13:
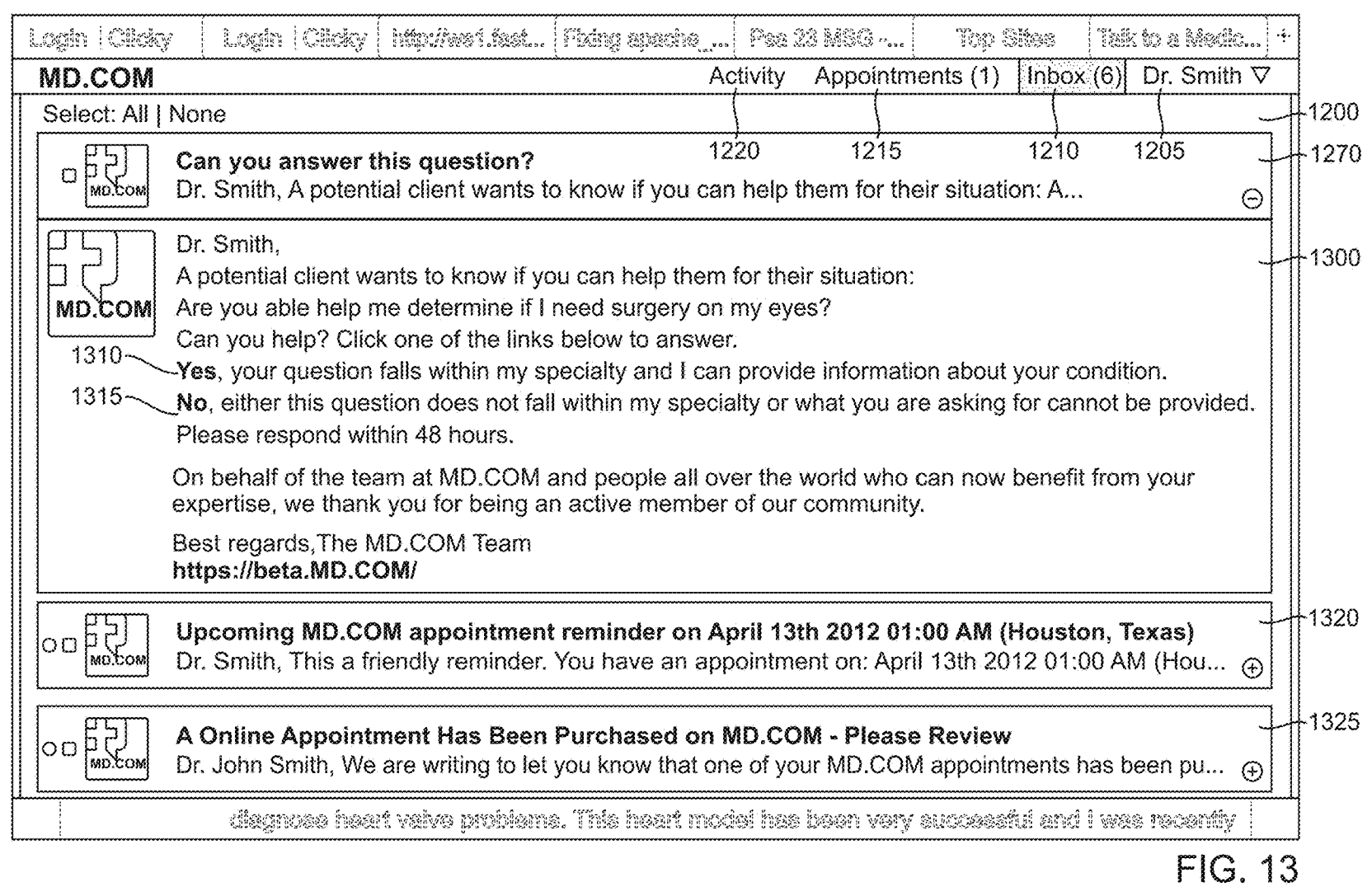

For example, in FIG. 13, selection or designation of the Question message 1270 expands the Question message 1270 in the Message Inbox 1225. By expanding the Question message 1270, the subsequent message 1320, 1325 in the Message Inbox 1225 can be shifted down or collapsed. For example, the reminder message 1230 informing the professional of an upcoming appointment can be shifted down or collapsed. Similarly, a new appointment message 1325 informing the professional of a new appointment purchased for the professional can also be shifted down or collapsed.

In FIG. 12, the Question message 1270 has been expanded to display the body 1300 of the Question message 1270. In FIG. 13, the body 1300 of the Question message 1270 can include the question 1305 ("Are you able to help me determine if I need surgery on my eyes?") asked by the client of FIG. 8. Also shown in FIG. 13, the body 1300 of the Question message 1270 can include confirmation/rejection option 1310, 1315 by which the professional can respond to the client's question. For example, the confirmation/negation option 1310, 1315 can include selectable text corresponding to an affirmative response 1310 (for example, a selectable "yes") and a negative response 1315 (for example, a selectable "no"). The professional can select one of the confirmation/rejection options 1310, 1315, which thereby instructs the server 101 to send a corresponding response to the client who sent the Question message 1270. If the professional selects the rejection option or the negative response 1315, a notification message 1400, such as the one illustrated in FIG. 14, can be transmitted to the client.

Figure 14:
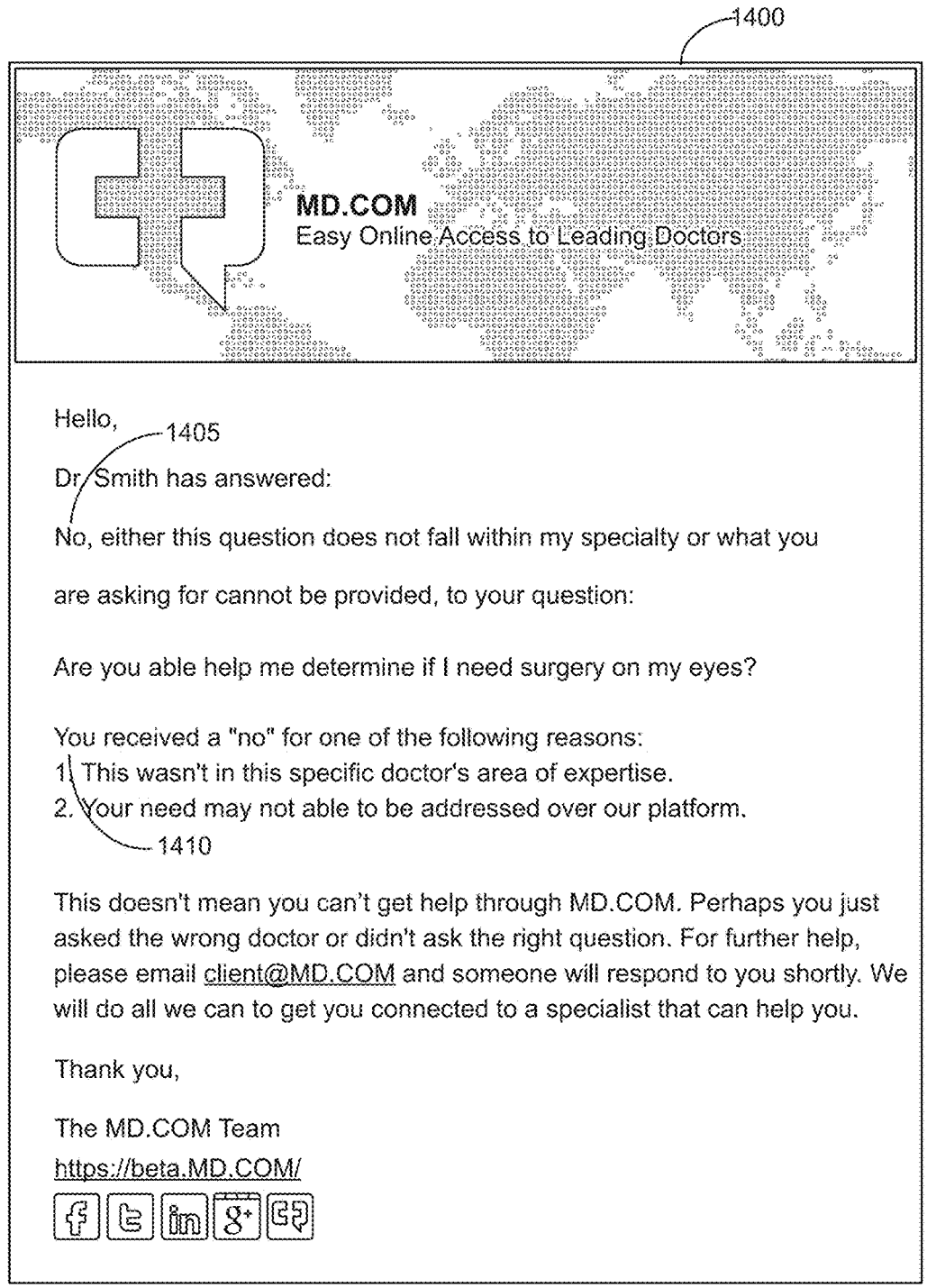

In FIG. 14, the notification message 1400 can include notifying text 1405 informing the client that the professional has answered his or her question 805 in the negative. Additionally, the notification message can include explanatory text 1410 explaining why the professional has answered his or her question in the negative. For example, the explanatory text 1410 can indicate that the client's question 805 fell outside the professional's area of expertise.

Figure 15:
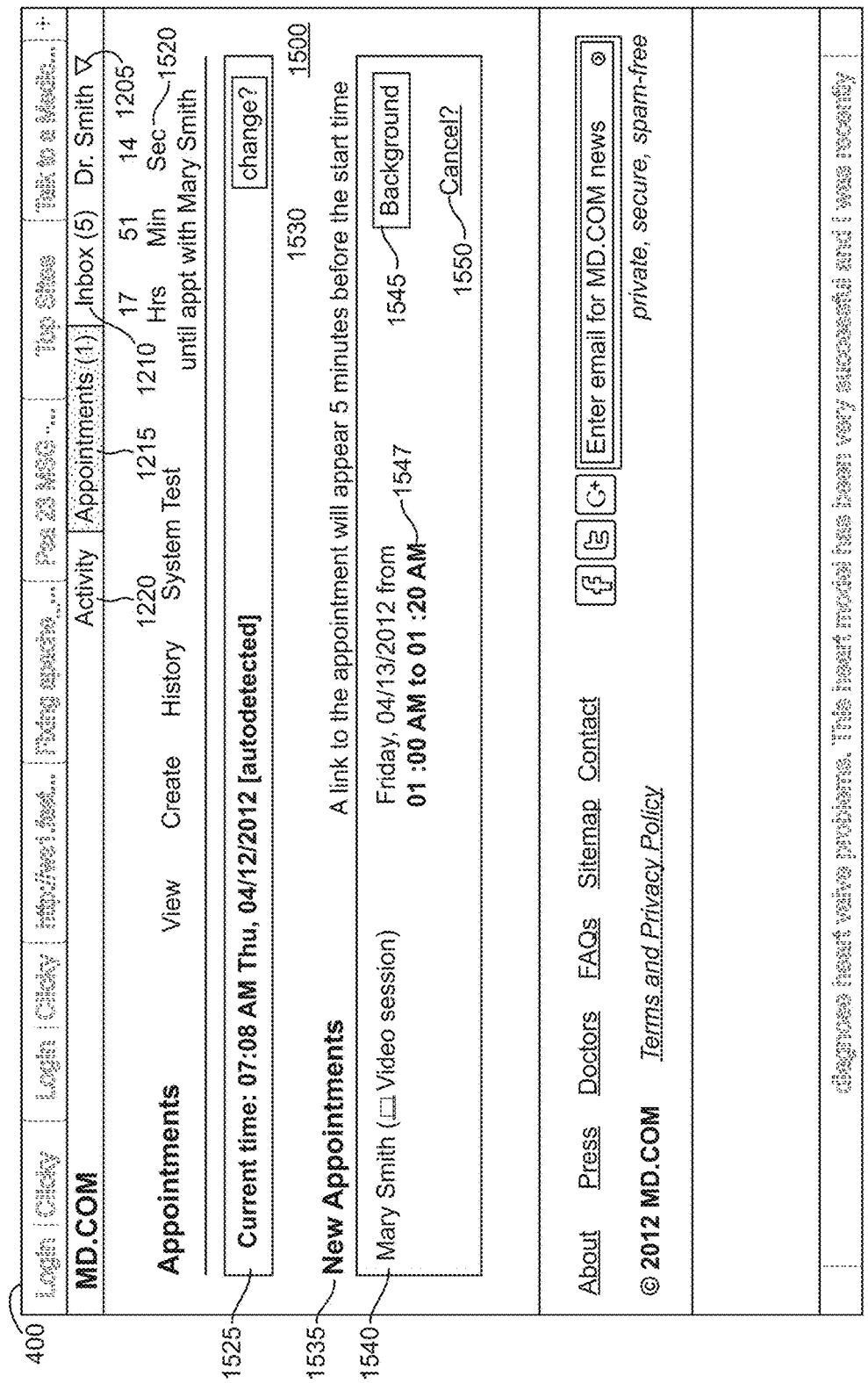

FIG. 15 illustrates an Appointments page 1500 that can be displayed to the professional in response to a selection of the Appointments tab 1215 of the professional's home page. The Appointments page 1500 can display the current time 1525. A change button 1530 can be included to change a time zone of the professional. As illustrated in FIG. 15, the Appointments page 1500 can include options including View 1505, Create 1510, and History 1515. The View option 1505 can be selected to display timeslots and appointments the professional has designated as being available to accept or conduct virtual consultations. The Create option 1510 can be selected to create or open new timeslots or options that the professional is available to accept or conduct virtual consultations. The History option 1515 can be selected to display prior or past virtual consultations conducted by the professional.

In FIG. 15, when the professional selects the Appointments tab 1215, the default page displayed can be a page containing new appointments, pending appointments, upcoming appointments, or any combination thereof. Specifically, in FIG. 15, the Appointments page 1500 can display the new appointments 1535 for the professional. For example, under the New Appointments 1535, the upcoming appointment with the client Mary Smith 1540 is displayed. In FIG. 12, the upcoming appointment can include the date and time 1547 of the appointment, a background option 1545 and a cancel option 1550. The background option 1545 can be selected to retrieve the client's information which the professional can study prior to the scheduled appointment. Such client information can include any documents uploaded by the client. For example, the client information can include client forms, prior diagnoses, prior order or judgments, videos, audio recordings, photos, x-rays, medical records, legal records, financial records, or any other documents or files which may be helpful to the professional in properly evaluating or consulting with the client. The cancel option 1550 can be selected to cancel the appointment with the client. By selecting the cancel option 1550 a notification can be transmitted to the client that the professional has canceled the appointment. In at least one embodiment, when the professional cancels the appointment, the professional can have the option to suggest a new appointment or reschedule the appointment.

Also illustrated in FIG. 15, a timer or countdown clock 1520 can be displayed. The timer or countdown clock 1520 can provide a timer or countdown until the next appointment of the professional.

FIG. 16 illustrates a GUI 1625 in which the professional can accept, opt-in, or decline professional insurance coverage for any or all virtual consultations conducted in the virtual professional community. Specifically, in FIG. 16, an Account page 1600 is displayed in response to a selection of the accounts setting tab 1205 of the professional's home page. In FIG. 16, the Account page 1600 includes a General Tab 1605, a Search Criteria Tab 1610, a Financial Tab 1615, and a Settings Tab 1620. The General Tab 1605 can be selected to display general information such as biographical information of the professional. The professional can edit the general information associated with the General Tab 1605. The Search Criteria Tab 1610 can be selected to display one or more search terms generated by the server 101, contained in the search terms database 110, or both. In the Search Criteria Tab 1610 the professional can select search terms that the professional associates with his expertise and experience. Additionally, the Search Criteria Tab 1610 can include an option by which the professional can manually enter search terms that the professional desires to associate with this expertise and experience. By allowing the professional to designate the search criteria and search terms that are related to his expertise and experience, the search results generated by the server 101 in response to client queries can have an increase robustness and focus. The Settings Tab 1620 can be selected to display and edit any settings associated with the professionals home page or account. For example, the Settings Tab 1620 can include display setting, home page settings, user credentials, contact information, system configurations, preferences or any other similar setting which the professional can modify or edit.

In FIG. 16, the Financial Tab 1615 has been selected an Appointment Rate page 1631 can be displayed. The Appointment Rate page 1631 can display a current rate 1630 the professional charges for virtual consultations. In FIG. 16, the professional can edit or modify his rate 1630 by entering or modifying the amount in the editable Rate field 1632. Also illustrated in FIG. 16, the Appointment Rate page 1631 can include a professional insurance coverage 1635. The professional insurance coverage 1635 can include a professional liability insurance, a medical malpractice insurance, a legal malpractice insurance, or any other professional insurance coverage. In FIG. 16, the professional insurance coverage 1635 can display the terms and conditions 1637 of the professional insurance coverage. As discussed above, the professional insurance coverage 1635 can include a coverage amount 1639. The coverage amount 1639 can be based at least in part on one of a specialization of the professional. Also illustrated in FIG. 16, the professional insurance coverage 1635 can include a coverage period 1633. The coverage period 1633 can correspond to the duration of the virtual consultation or can be a fixed pre-determined duration set by one or more of the professional, an administrator of the virtual professionals community, an underwriter of the professional insurance coverage, a professional insurance coverage provider, or any other person or entity associated with providing the professional with the professional insurance coverage 1635. As illustrated in FIG. 16, selectable options including at least one of an opt-in or acceptance option 1640 and an opt-out or decline option 1645 for accepting or declining the professional insurance coverage 1635. In FIG. 16, the professional can be required to select one of the opt-in or acceptance option 1640 and the opt-out or decline option 1645. After the professional selects one of the opt-in or acceptance option 1640 and the opt-out or decline option 1645, the professional can select a Save option 1650, for saving the Appointment Rate 1632 and professional insurance coverage selection 1645, 1650. By selecting the Save option 1650, the Appointment Rate 1632 and professional insurance coverage selection 1645, 1650 can be applied to all virtual consultations conducted by the professional.

In other embodiments, the professional insurance coverage 1635 can be selected on a per virtual consultation basis. That is, the professional can opt-in or opt-out of the professional insurance coverage 1635 each time the professional initiates the virtual consultation. For example, prior to entering or accessing the virtual appointment or consultation interface, a notification can be displayed or presented to the professional requesting their selection to accept or decline the professional insurance coverage 1635. In such an embodiment, the professional may not initiate the virtual consultation or access the virtual appointment or consultation interface until the professional accepts or declines the professional coverage 1635.

Additionally, while FIG. 16 illustrates a single coverage amount for every virtual consultation conducted by the professional, in other embodiments, the coverage amount can vary. For example, the coverage amount can be based on at least in part on one or more of the problem, the symptom, the disease, the specialized professional practice, or any other criteria of the search query or request. The coverage amount can also be based on the actual specialization of the professional, a duration of the virtual consultation, an appointment rate, or any other factor by which the coverage amount can be calculated.

Figure 17:
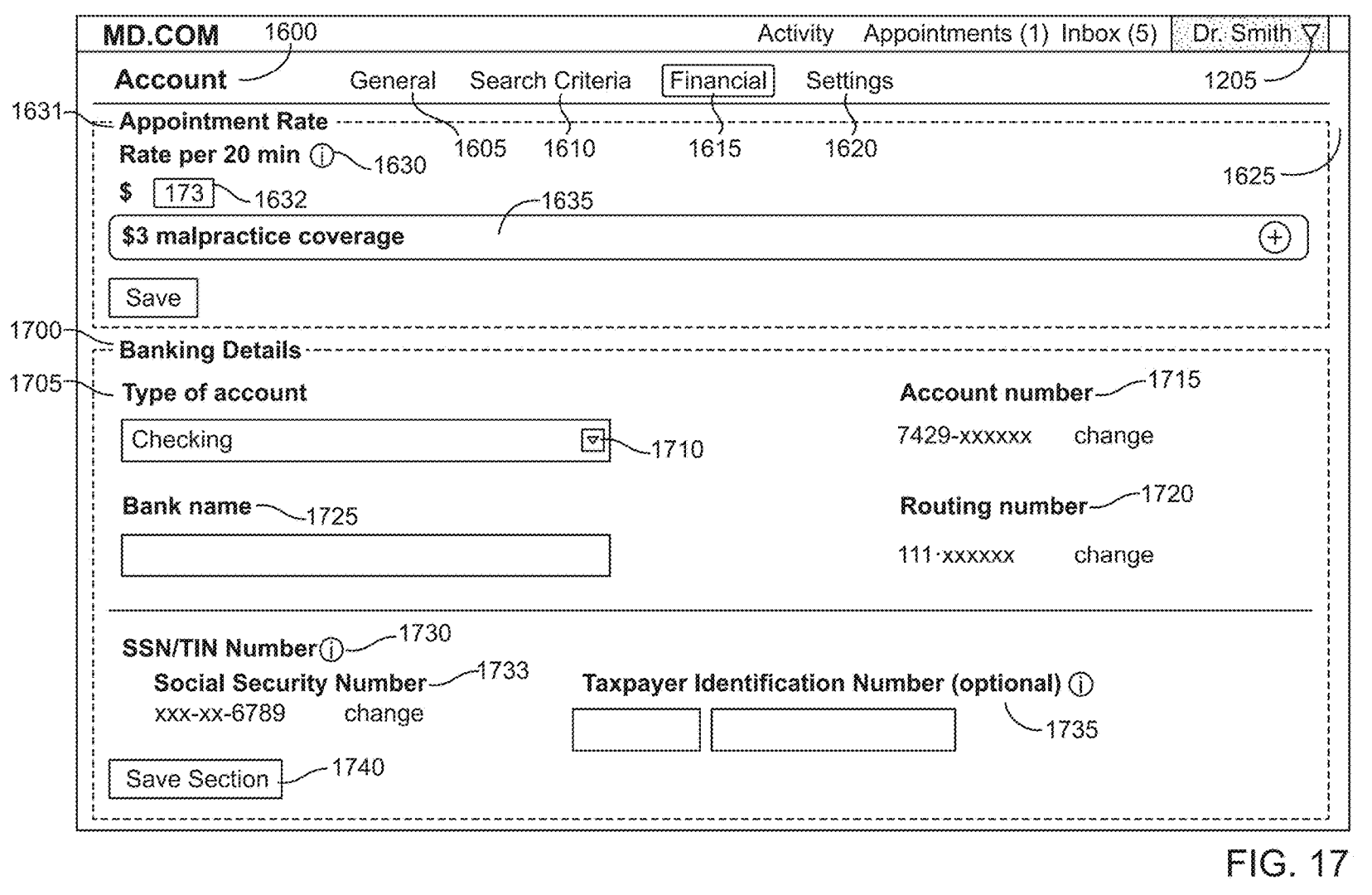

FIG. 17 illustrates the Account Page 1600 of the professional's home page, where the professional insurance coverage 1635 has been collapsed and the information associated with the professional's banking details section 1700 is displayed. In FIG. 17, the banking details section 1700 can include a type of account 1705. The type of account 1705 can be selected form a pull down menu 1710 or any other menu by which the professional can select the type of account 1705 by which payments can be made. The Banking Details section 1700 can also include a Bank Name filed 1725, an Account Number field 1715, and a Routing Number field 1720 by which the professional can input such information. The Banking Details Section 1700 can also include a Tax Information section 1730. The Tax Information section 1730 can include a Social Security Number field 1733 and a Tax Payer Identification Number filed 1735 by which the professional can input the appropriate information. The Banking Details section 1700 can also include a Save Section option 1740 by which the user can select the option 1740 to save the information inputted in the Banking Details section 1700.

Figure 18:
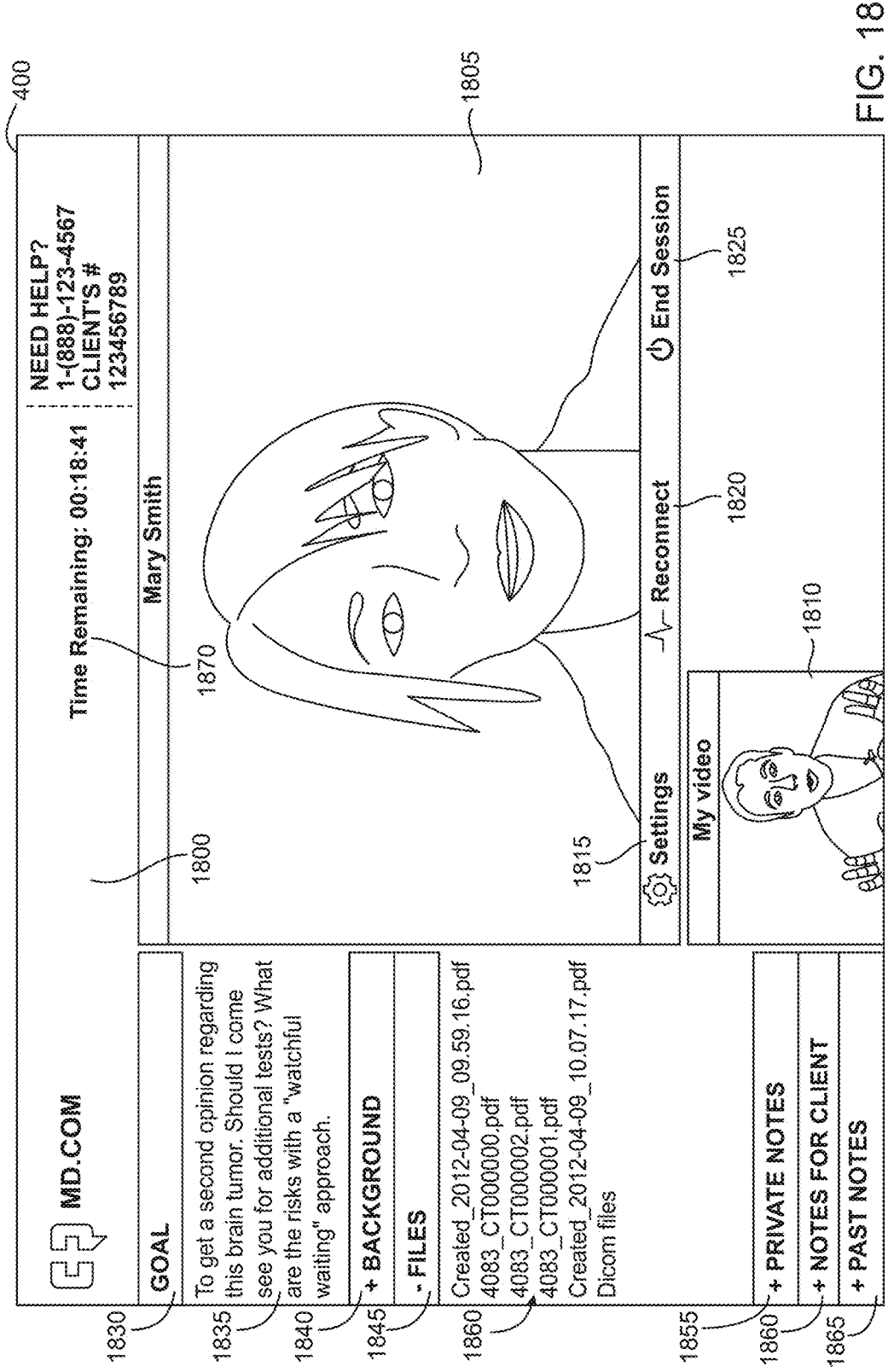
FIGS. 18-20 are example screenshots of a virtual consultation graphical user interface presented to a professional during the virtual consultation, in accordance with an example embodiment of the present disclosure.
Figure 19:
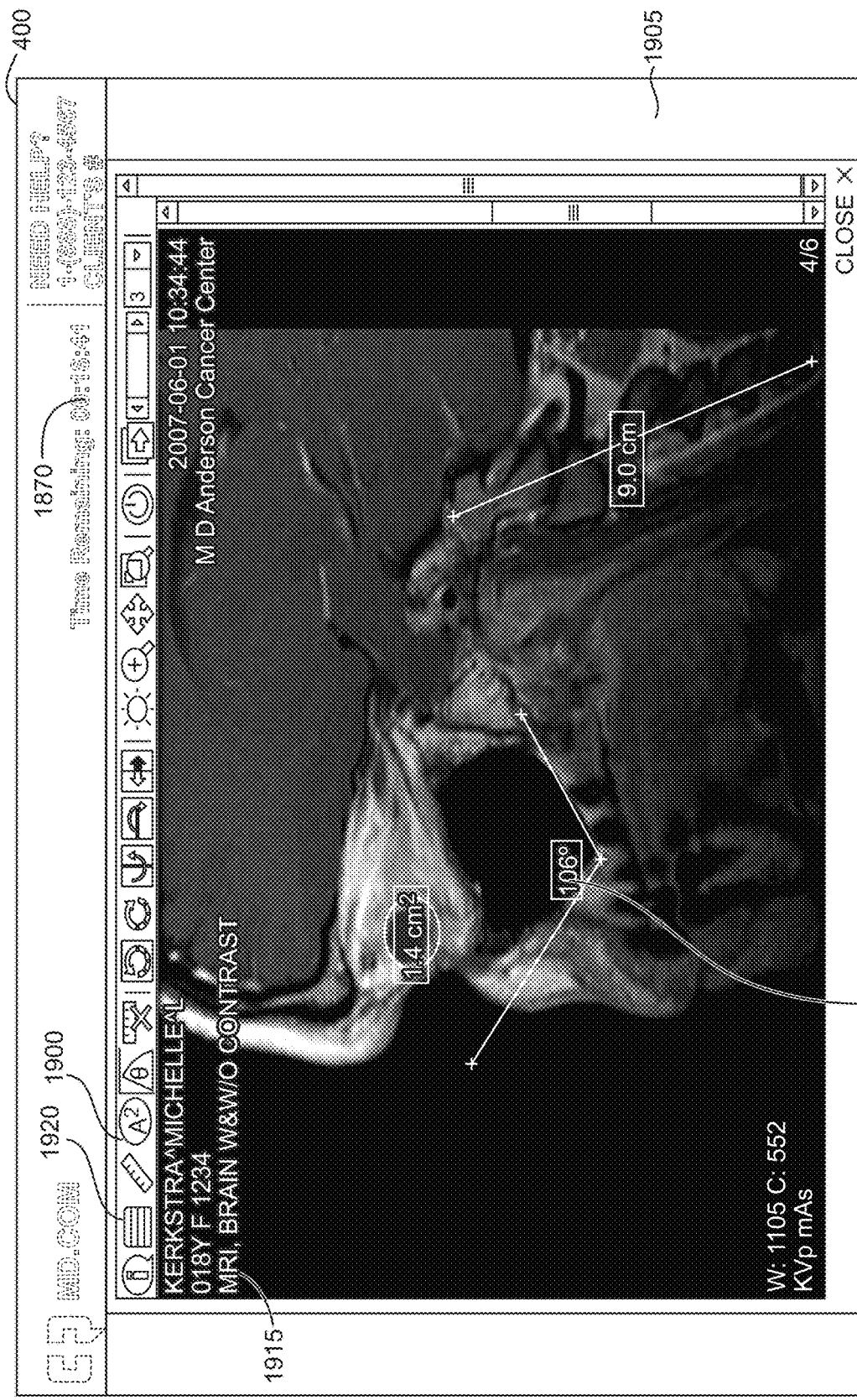
Figure 20:
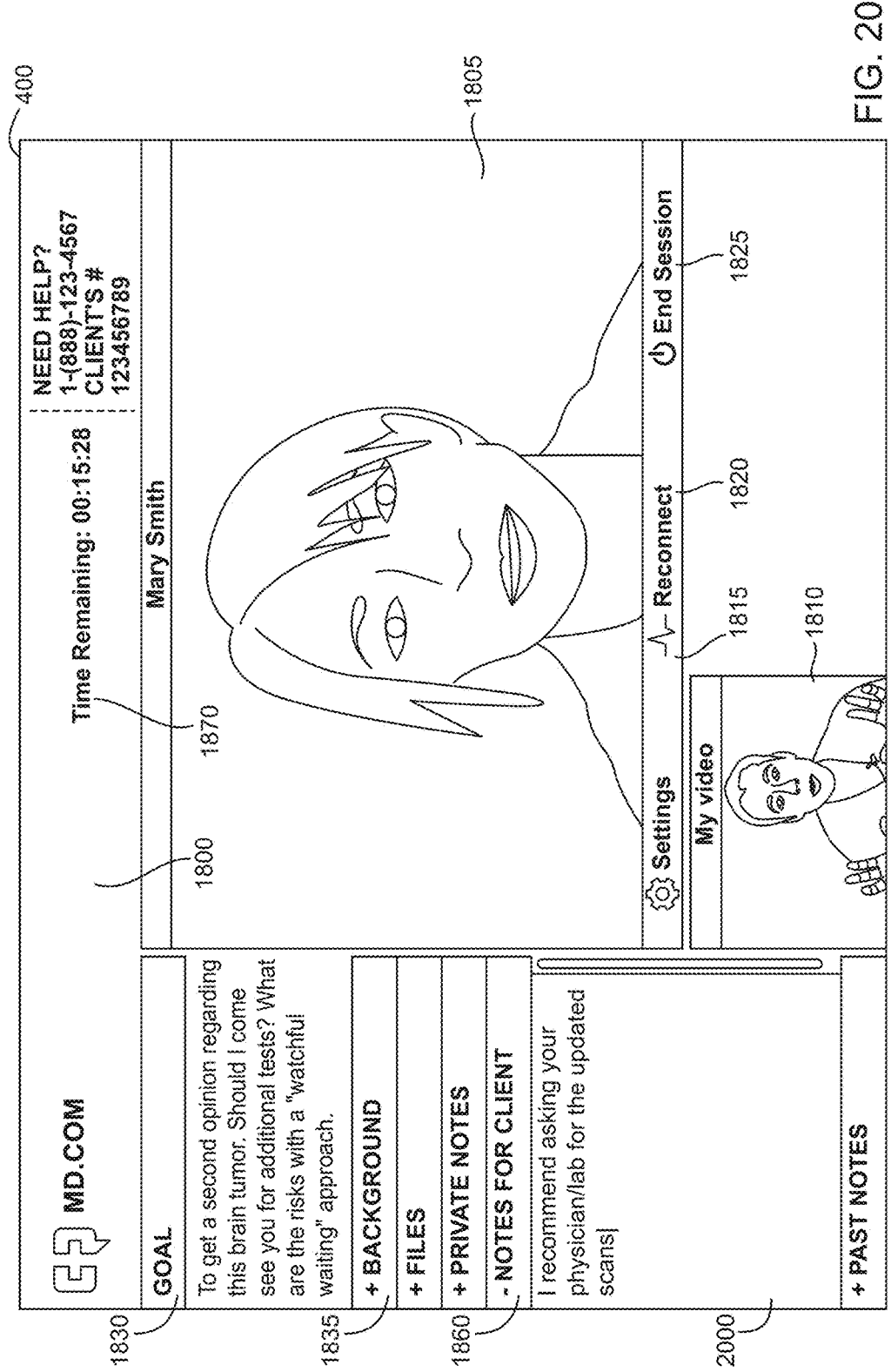
Figure 21:
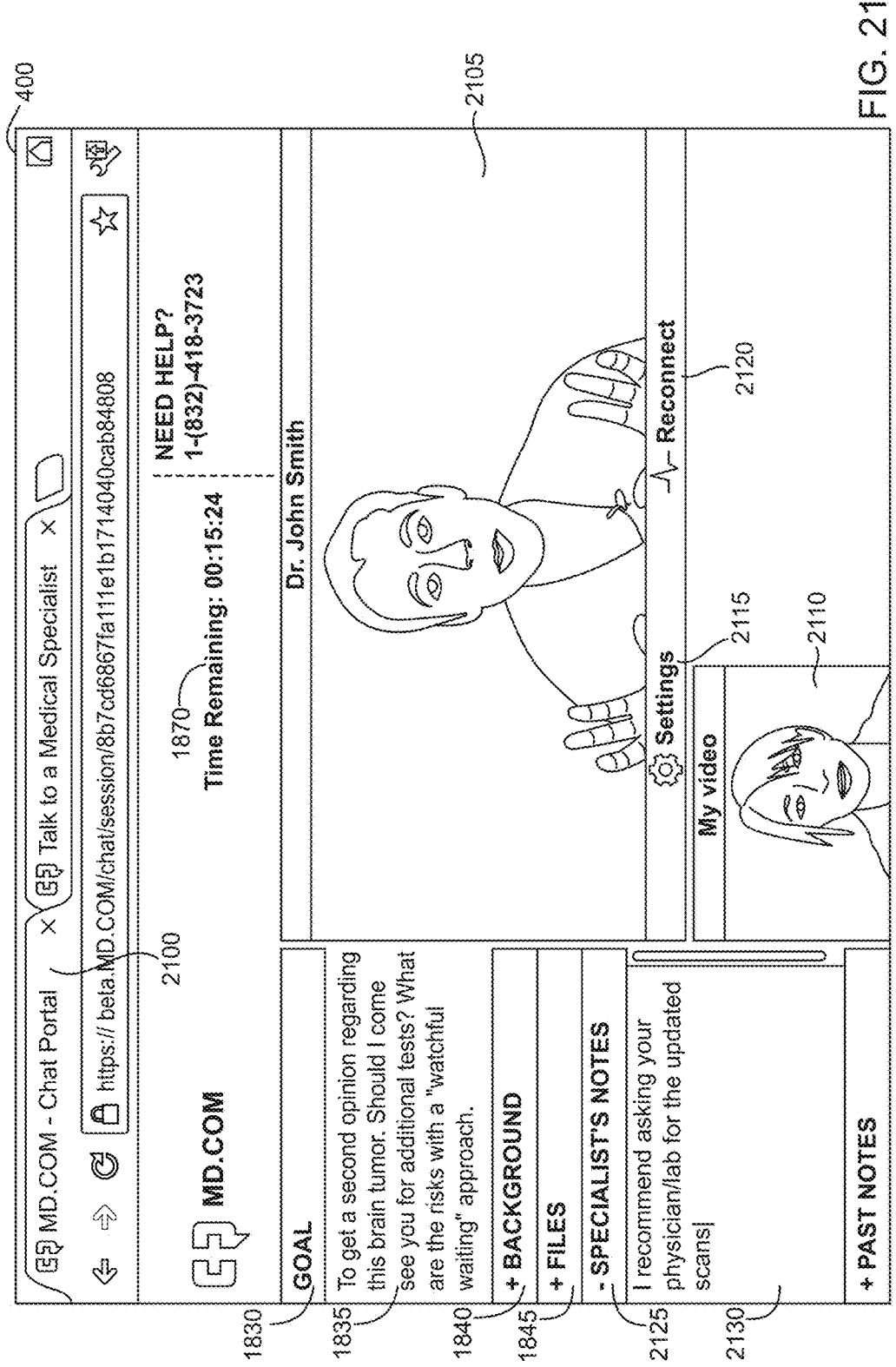
FIG. 21 is an example screenshot of a virtual consultation graphical user interface presented to a client during the virtual consultation, in accordance with an example embodiment of the present disclosure.

FIGS. 18-21 illustrate example GUIs 400 associated with the virtual consultation or application interface established between the client electronic device 150*a-c* and the professional electronic device 175*a-b*. FIGS. 18-20 illustrate the professional's virtual consultation user interface 1800 displayed at the professional electronic device 175*a-c*. FIG. 21 illustrates the client's virtual consultation user interface 2100 displayed at the client electronic device 150*a-c*. Specifically, FIGS. 18-21 illustrate a virtual consultation that is conducted via web-based videoconference.

In FIG. 18-21, the professional's virtual consultation user interface 1800 includes a client's video feed 1805, the professional's video feed 1810, and a plurality of information 1830, 1840, 1845, 1850, 1855, 1860, 1865 associated with the virtual consultation. As illustrated in FIGS. 18 and 20, the client's video feed 1805 can be displayed in a primary portion of the professional's virtual consultation user interface 1800 such that the client's video feed 1805 occupies a majority of the professional's screen.

The information associated with the virtual consultation can include a Goal Section 1830 describing the client's goal for the virtual consultation. Detailed goal text 1835 can be displayed beneath the Goal Section 1830. The detailed goal text 1835 can be generated by the client, an administrator of the virtual professionals community, or automatically generated by the processor 101 of the virtual professionals community based on the client's search query.

The Background Section 1840 can be selected to display, to the professional, background information such as those described above. For example, the Background Section 1840 can list the symptoms, problems, diseases, issues, etc. associated with the client.

As illustrated in FIG. 18, the professional's virtual consultation user interface 1800 can include a Private Notes section 1855. The Private Notes section 1855 can include any notes that the professional creates during or prior to the virtual consultation. The Private Notes section 1855 can be hidden from the client. For example, the client's virtual consultation user interface 2100 (shown in FIG. 21) may not include the Private Notes section.

The professional's virtual consultation user interface 1800 can also include a Notes for Client section 1860. The Notes for Client section 1860 can include any notes that the professional creates during or prior to the virtual consultation and that the professional desires to share with the client. In at least one embodiment, as the professional enters notes 2000 (shown in FIG. 20) in the Notes for Client section 1860, the notes 200 can appear in a corresponding section (for example, Specialist's Notes section 2125 of the client's virtual consultation user interface 2100). That is, the client can view the professional's notes in real-time as the professional enters notes in the Notes for Client section 1860.

The professional's virtual consultation user interface 1800 can also include a Past Notes section 1865. In FIGS. 18 and 20, the Past Notes section 1865 can also appear in the client's virtual consultation user interface 2100 (shown in FIG. 21). The Past Notes section 1865 can include any notes created by the professional or client during a prior virtual consultation between the client and the professional.

As illustrated in FIGS. 18 and 20, the professional's virtual consultation user interface 1800 can also include a Settings option 1815 for adjusting any settings associated with the virtual consultation. For example, the settings can include a display size, a resolution, a bandwidth availability, a volume, video settings, audio settings, color settings, or any other similar settings associated with the virtual consultation. A reconnect option 1820 can also be included if the professional electronic device 175*a-b* loses or is disconnected from the virtual consultation or appointment interface.

The Files Section 1845 can include any documents or files, uploaded by the client or the professional, that are associated with the client. In FIG. 18, the Files Section 1845 has been expanded to display the one or more files 1850 associated with the client. For example, the files can include any files described above, such as medical records, legal records, financial records, property records, x-rays, videos, photos, audio files, or any other files associated with the client which may be helpful to the professional in evaluating, diagnosing, or otherwise consulting with the client.

In at least one embodiment, for example the embodiment illustrated in FIG. 19, the professional or the client can select one of the files 1850 in the Files Section 1845. In response to a selection the file a viewer 1900 can be displayed or initiated. In FIG. 19, the viewer 1900 can be displayed on top of or overlaid on each of the professional's virtual consultation user interface 1800 and the client's virtual consultation user interface 2100. In FIG. 19, a Magnetic resonance imaging (MRI) file 1905 has been selected and displayed in the viewer 1900. According to one embodiment, the viewer 1900 can display any type of file. That is, the original files can be opened rather than being converted to another type of file. By allowing the viewer 1905 to read any file, a quicker and more robust virtual consultation can be provided, as the client and the professional will not be limited to the types of files that can be displayed during the virtual consultation. While FIG. 19 illustrates that the viewer 1905 can read and display any type of file without converting the file to another file, in other embodiments, the viewer 1905 can convert any of the files contained in the File Section 1845 into a file type or format that is easily or readily readable by the viewer 1905.

In FIG. 19, the viewer 1905 can allow either or both of the client and the professional to annotate or otherwise mark the MRI 1905 as it is displayed on both the professional's virtual consultation user interface 1800 and the client's virtual consultation user interface 2100. For example, the professional can select a tool from the annotation toolbar 1920 of the viewer. In FIG. 19, the professional can select a ruler tool to measure items contained in the MRI 1905. Specifically, in FIG. 19, the professional can add annotations 1910 (such as measurements, notes, or any other markings) to the MRI 1905. As the professional address such annotations 1910, the annotations 1910 will substantially simultaneously appear on the client's virtual consultation user interface 2100. That is, any annotation 1910 made by the professional will appear on the client's virtual consultation user interface 2100 in real-time.

Also illustrated in FIG. 19, the professional or the client can select a tool from the tool bar 1920 to add text 1915 to the MRI 1905. In FIG. 19, the client has added text 1915 to the MRI 1905, wherein the text includes the client's name and other identification information. Again, the notations made by the client at the client's virtual consultation user interface 2100 can appear on the professional's virtual consultation interface 1800 in real-time.

In at least one embodiment, either or both of the client and professional can manipulate the view and orientation of the MRI 1905. For example, the MRI 1905 can be rotated, zoomed in, re-sized, cropped, brightened, or otherwise manipulated to alter an appearance of the MRI 1905. Again, any manipulations made at the client's virtual consultation user interface 2100 will be made or will appear on the professional's virtual consultation interface 1800 in real-time, and vice versa.

A notable difference between the professional's virtual consultation user interface 1800 and the client's virtual consultation user interface 2100 is that the professional's virtual consultation user interface 1800 includes an end session option 1825 that is not included in the client's virtual consultation user interface 2100. As discussed above, access to the virtual appointment or the virtual consultation by the client electronic device 150*a-c* can be controlled by a detected connection of the professional electronic device 175*a-b* to the virtual appointment or the virtual consultation (for example, the appointment interface or virtual consultation interface). For example, access to the virtual appointment or the virtual consultation by the client electronic device 150*a-c* can be controlled a disconnection of the professional electronic device 175*a-b* from the communication interface (for example, the appointment interface or virtual consultation interface) such that when the disconnection of the professional electronic device 175*a-b* is detected, access to the virtual appointment by the client electronic device 150*a-c* is terminated.

In FIGS. 18-21, if the professional selects the disconnect option 1825 at the professional's virtual consultation user interface 1800, the virtual consultation can be terminated, and the client electronic device 150*a-c* can be automatically disconnected from the virtual consultation interface. In at least one embodiment, the virtual consultation interface can be automatically terminated when a countdown clock or timer 1870 provided on either or both of the professional's virtual consultation user interface 1800 and the client's virtual consultation user interface 2100 expires.

In other embodiments, a warning can be displayed to either or both of the professional's virtual consultation user interface 1800 and the client's virtual consultation user interface 2100 that the allotted duration of the virtual consultation is about to expire. The warning (not shown) can include a selectable option presented the client's virtual consultation user interface 2100 to purchase additional time. Similarly, the warning can include a selectable option presented to the professional's virtual consultation user interface 1800 to extend the allotted time for the virtual consultation. In either embodiment, the client electronic device's 150*a-c* connection to the virtual consultation interface can depend on the professional electronic device's 175*a-b* connection to the virtual consultation interface.

Although not illustrated, prior to accessing the virtual consultation, the client's virtual consultation user interface 2100 can be a waiting room GUI. The waiting room GUI can be displayed when the professional has not yet connected to the virtual consultation, as the professional electronic device's 175a-b connection to the virtual consultation interface controls the client electronic device's 150a-c access to the virtual consultation. In the waiting room GUI, one or more advertisements, photos, videos, or other graphical information can be displayed. Such graphical information can be selected and displayed based upon the search query of the client, any information or data associated with the upcoming virtual consultation, or any other data or information associated with the client or the professional with whom the client will be conducting the virtual consultation.

Examples within the scope of the present disclosure may also include tangible and/or non-transitory computer-readable storage media for carrying or having computer-executable instructions or data structures stored thereon. Such non-transitory computer-readable storage media can be any available media that can be accessed by a general purpose or special purpose computer, including the functional design of any special purpose processor as discussed above. By way of example, and not limitation, such non-transitory computer-readable media can include RAM, ROM, EEPROM, CD-ROM or other optical disk storage, magnetic disk storage or other magnetic storage devices, or any other medium which can be utilized to carry or store desired program code means in the form of computer-executable instructions, data structures, or processor chip design. When information is transferred or provided over a network or another communications connection (either hardwired, wireless, or combination thereof) to a computer, the computer properly views the connection as a computer-readable medium. Thus, any such connection is properly termed a computer-readable medium. Combinations of the above should also be included within the scope of the computer-readable media.

Computer-executable instructions include, for example, instructions and data which cause a general purpose computer, special purpose computer, or special purpose processing device to perform a certain function or group of functions. Computer-executable instructions also include program modules that are executed by computers in stand-alone or network environments. Generally, program modules include routines, programs, components, data structures, objects, and the functions inherent in the design of special-purpose processors, etc. that perform particular tasks or implement particular abstract data types. Computer-executable instructions, associated data structures, and program modules represent examples of the program code means for executing steps of the methods disclosed herein. The particular sequence of such executable instructions or associated data structures represents examples of corresponding acts for implementing the functions described in such steps.

Those of skill in the art will appreciate that other examples of the disclosure may be practiced in network computing environments with many types of computer system configurations, including personal computers, hand-held devices, multi-processor systems, microprocessor-based or programmable consumer electronics, network PCs, minicomputers, mainframe computers, and the like. Examples may also be practiced in distributed computing environments where tasks are performed by local and remote processing devices that are linked (either by hardwired links, wireless links, or by a combination thereof) through a communications network. In a distributed computing environment, program modules may be located in both local and remote memory storage devices.

The various examples described above are provided by way of illustration only and should not be construed to limit the scope of the disclosure. For example, the principles herein apply not only to a smartphone device but to other devices capable of detecting communications such as a laptop computer. Those skilled in the art will readily recognize various modifications and changes that may be made to the principles described herein without following the example embodiments and applications illustrated and described herein, and without departing from the scope of the disclosure.

We claim:

1. A computer-implemented method comprising:
providing a server, the server communicatively coupled to a first electronic device by a network, one or more other electronic devices by the network, a database configured to store data associated with a plurality of professionals and peer performance ratings, the server providing a virtual appointment application for installation on the first electronic device and a second electronic device, the virtual appointment application configured to establish a communication interface between the first electronic device and the second electronic device;
receiving, from the virtual appointment application installed on the first electronic device, data associated with a plurality of professionals, the data including a specialty descriptive of one or more of the plurality of professionals;
storing, in the database, the data associated with the plurality of professionals;
receiving, from one or more professional electronic devices, peer performance reviews for the plurality of professionals, the peer performance reviews comprising data generated from an electronic survey including a rating component and a text component, the electronic survey performed over the one or more professional electronic devices;
storing, in the database, the peer performance reviews;
receiving, from the virtual appointment application installed on the first electronic device, a search request for one or more relevant professionals, the search request including search criteria;
searching the data associated with the plurality of professionals and the text components of the peer performance reviews, for one or more relevant professionals based on the search criteria;
ranking, at the server, the one or more relevant professionals based on the rating component of the peer performance reviews and the search request; and
transmitting, to the virtual appointment application installed on the first electronic device, a report of one or more ranked relevant professionals and a selectable option to book a virtual appointment with the one or more ranked relevant professionals, the report including relevant text components of the peer performance reviews of one or more of the ranked relevant professionals, the relevant text components determined based on the search request;
wherein the report comprises a navigable interface grouping each of the relevant text components of the peer performance reviews with at least one of a respective rate, cost, or price for conducting the virtual appointment, and wherein the groupings are ordered based on the rating component of the peer performance reviews.

2. The method of claim 1,
the data associated with a plurality of professionals received by providing a personal login for each of the plurality of professionals and receiving personal professional detail data associated with each login.

3. The method of claim 1,
the server receiving from the first electronic device a selection for one of the relevant professionals.

4. The method of claim 3,
the first electronic device being associated with a client and the second electronic device being associated with the selected professional.

5. The method of claim 4, wherein the communication interface between the first and second electronic devices includes video telecommunications.

6. The method of claim 1, wherein the criteria includes at least one search term.

7. The method of claim 1, wherein the plurality of professional are medical professionals.

8. The method of claim 1, wherein the specialty descriptive of one or more of the plurality of professionals is a medical specialty.

9. A system comprising:
a server including a processor and being communicatively coupled to a first electronic device by a network, one or more other electronic devices by the network, a database configured to store data associated with a plurality of professionals and peer performance ratings, and establishing a communication interface between the first electronic device and a second electronic device;
a virtual appointment application for installation on electronic devices; and
a non-transitory computer readable storage medium storing instructions for controlling the processor to:
receive, from the virtual appointment application installed on the first electronic device, data associated with a plurality of professionals, the data including a specialty descriptive of one or more of the plurality of professionals;
receive, from one or more professional electronic devices, peer performance reviews for the plurality of professionals, the peer performance reviews comprising data generated from an electronic survey including a rating component and a text component, the electronic survey performed over the one or more professional electronic devices;
receive, from the virtual appointment application installed on the first electronic device, a search request for selecting relevant professionals, the search request including search criteria;
conduct, at the server, a search of the received data and the text components of the peer performance reviews to select relevant professionals, the search based on the search criteria;
rank, at the server, the selected relevant professionals based on the rating component of the peer performance reviews and the search request; and
transmit, to the virtual appointment application installed on first electronic device, a report of one or more relevant professionals and a selectable option to book a virtual appointment with the one or more ranked relevant professionals, the report including relevant text components of the peer performance reviews of one or more of the ranked relevant professionals, the relevant text components determined based on the search request;
wherein the report comprises a navigable interface grouping each of the relevant text components of the peer performance reviews with at least one of a respective rate, cost, or price for conducting the virtual appointment, and wherein the groupings are ordered based on the rating component of the peer performance reviews.

10. The system of claim 9,
the data associated with a plurality of professionals received by providing a personal login for each of the plurality of professionals and receiving personal professional detail data associated with each login.

11. The system of claim 9,
the server receiving from the first electronic device a selection for one of the relevant professionals.

12. The system of claim 11,
the first electronic device being associated with a client and the second electronic device being associated with the selected professional.

13. The system of claim 12, wherein the communication interface between the first and second electronic devices includes video telecommunications.

14. A computer-implemented method comprising:
providing a server, the server communicatively coupled to a first electronic device by a network, a database configured to store data associated with a plurality of professionals, the server providing a virtual appointment application for installation on the first electronic device and a second electronic device, the virtual appointment application configured to establish a communication interface between the first electronic device and the second electronic device;
receiving, from one or more professional electronic devices, data associated with a plurality of professionals, the data including a specialty descriptive of one or more of the plurality of professionals and peer performance reviews comprising data generated from an electronic survey including a rating component and a text component, the electronic survey performed over the one or more professional electronic devices;
storing, in the database, the data associated with a plurality of professionals;
receiving, from the virtual appointment application installed on the first electronic device, a search request for one or more relevant professionals including search criteria;
searching, the data associated with the plurality of professionals and the text components of the peer performance reviews, for one or more relevant professionals based at least in part on the criteria;
selecting, at the server, a most relevant professional from the search; and
transmitting, to the virtual appointment application installed on the first electronic device, a notification of the selection, the notification including a confirmation/rejection option to book a virtual appointment with the selection and relevant text components of the peer performance reviews of one or more of the relevant professionals, the relevant text components determined based on the search request;
wherein the report comprises a navigable interface grouping each of the relevant text components of the peer performance reviews with at least one of a respective rate, cost, or price for conducting the virtual appointment, and wherein the groupings are ordered based on the rating component of the peer performance reviews.

15. The method of claim 14, further comprising
selecting the next most relevant professional from the search and transmitting a notification to the first electronic device in response to receiving a rejection of the previous notification.

16. The method of claim 14, further comprising receiving, from the first electronic device, a confirmation of selection of the most relevant professional from the search.

17. The method of claim 16, further comprising communicating the confirmation of selection to the second electronic device with a second confirmation/rejection option in response to receiving confirmation of selection from the first electronic device.

18. The method of claim 17, wherein the first electronic device is associated with a client and the second electronic device is associated with a professional.

\* \* \* \* \*